US009299155B2

(12) United States Patent
Farsiu et al.

(10) Patent No.: US 9,299,155 B2
(45) Date of Patent: Mar. 29, 2016

(54) SEGMENTATION AND IDENTIFICATION OF LAYERED STRUCTURES IN IMAGES

(71) Applicant: Duke University, Durham, NC (US)

(72) Inventors: Sina Farsiu, Durham, NC (US); Stephanie J. Chiu, Durham, NC (US); Cynthia A. Toth, Chapel Hill, NC (US); Joseph A. Izatt, Raleigh, NC (US); Xiao T. Li, Cumming, GA (US); Peter Christopher Nicholas, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 14/337,215

(22) Filed: Jul. 21, 2014

(65) Prior Publication Data

US 2014/0334703 A1 Nov. 13, 2014

Related U.S. Application Data

(62) Division of application No. 13/010,448, filed on Jan. 20, 2011, now Pat. No. 8,811,745.

(60) Provisional application No. 61/296,653, filed on Jan. 20, 2010.

(51) Int. Cl.
*G06K 9/34* (2006.01)
*G06T 7/00* (2006.01)
*A61B 5/00* (2006.01)

(52) U.S. Cl.
CPC ............. *G06T 7/0081* (2013.01); *A61B 5/0066* (2013.01); *G06K 9/34* (2013.01); *G06T 7/0093* (2013.01); *A61B 5/7203* (2013.01); *G06T 2207/10004* (2013.01); *G06T 2207/30041* (2013.01)

(58) Field of Classification Search
None
See application file for complete search history.

(56) References Cited

U.S. PATENT DOCUMENTS

| 2007/0086647 | A1* | 4/2007 | Grady | G06T 7/0083 |
| | | | | 382/154 |
| 2008/0019587 | A1* | 1/2008 | Wilensky | G06T 7/0083 |
| | | | | 382/159 |
| 2010/0202677 | A1* | 8/2010 | Imamura | G06T 7/0012 |
| | | | | 382/131 |

OTHER PUBLICATIONS

Intra-retinal segmentation—images, Mishra et al., Optic Express 23719, Published Dec. 11, 2009, pp. 1-10.*
Intraretinal layer segmentation—search., Garvin et al., I EEE, 0278-0062, 2008, pp. 1495-1505.*
Graph cuts segmentation—medical images, Jacquot et al., I EEE,978-0-7695-3122, 2008, pp. 631-635.*

(Continued)

*Primary Examiner* — Jayesh A Patel
(74) *Attorney, Agent, or Firm* — Olive Law Group, PLLC

(57) ABSTRACT

Disclosed herein are systems and method for segmentation and identification of structured features in images. According to an aspect, a method may include representing an image as a graph of nodes connected together by edges. For example, the image may be an ocular image showing layered structures or other features of the retina. The method may also include adding, to the graph, nodes adjacent to nodes along first and second sides of the graph. The added nodes may have edge weights less than the nodes along the first and second sides of the graph. Further, the method may include assigning start and end points to any of the added nodes along the first and second sides, respectively. The method may also include graph cutting between the start and end points for identifying a feature in the image.

5 Claims, 35 Drawing Sheets

(56) References Cited

OTHER PUBLICATIONS

Fernandez et al., Automated Detection of Retinal Layer Structures on Optical Coherence Tomography Images, Optics Express, vol. 13, No. 25, Dec. 12, 2005, U.S.

Ishikawa et al., Macular Segmentation with Optical Coherence Tomography, Investigative Ophthalmology & Visual Science, vol. 46, No. 6, Association for Research in Vision and Ophthalmology, Jun. 2005, U.S.

Fabritius et al., Automated Segmentation of the Macula by Optical Coherence Tomography, Optics Express, vol. 17, No. 18, Aug. 31, 2009, U.S.

Yazdanpanah et al., Segmentation of Intra-Retinal Layers from Optical Coherence Tomography Images Using an Active Contour Approach, IEEE, 2010, U.S.

Farsiu et al., Fast Detection and Segmentation of Drusen in Retinal Optical Coherence Tomography Images, Ophthalmic Technologies XVIII, Proc. of SPIE vol. 6844, 2008, U.S.

Mishra et al., Intra-Retinal Layer Segmentation in Optical Coherence Tomography Images, Optics Express, vol. 17, No. 26, Dec. 21, 2009, U.S.

Haeker et al., Automated Segmentation of Intraretinal Layers from Macular Optical Coherence Tomography Images, Society of Photo-Optical Instrumentation Engineers, 2007, U.S.

Garvin et al., Automated 3-D Intraretinal Layer Segmentation of Macular Spectral-Domain Optical Coherence Tomography Images, IEEE Transactions on Medical Imaging, vol. 28, No. 9, Sep. 2009, U.S.

Dijkstra, A Note on Two Problems in Connexion with Graphs, Cambridge University Press, 1897, vol. 13, p. 26-8, U.K.

Niemeijer et al., Vessel Segmentation in 3D Spectral OCT Scans of the Retina, Medical Imaging 2008, Image Processing, Proc. of SPIE, vol. 6914, 2008, U.S.

Shi et al., Normalized Cuts and Image Segmentation, IEEE Transactions on Pattern Analysis and Machine Intelligence, vol. 22, No. 8, Aug. 2000, U.S.

Tolliver et al., Unassisted Segmentation of Multiple Retinal Layers via Spectral Rounding, Presented in ARVO 2008 Annual Meeting, Fort Lauderdale, Florida, U.S., Apr. 2008.

Elias et al., A Note on the Maximum Flow Through a Network, IRE Transactions on Information Theory, 1956.

The Age-Related Eye Disease Study Research Group, The Age-Related Eye Disease Study System for Classifying Age-Related Macular Degeneration From Stereoscopic Color Fundus Photographs: The Age-Related Eye Disease Study Report No. 6, Elsevier Service Inc., vol. 132, No. 5, 2001, U.S.

Lu et al., Automated Layer Segmentation of Optical Coherence Tomography Images, IEEE Transactions on Biomedical Engineering, vol. 57, No. 10, Oct. 2010, U.S.

Otsu, A Threshold Selection Method from Gray-Level Histograms, IEEE Transactions on Systems, Man, and Cybernetics, vol. SMC-9, No. 1, Jan. 1979, U.S.

Takeda et al., Kernel Regression for Image Processing and Reconstruction, IEEE Transactions on Image Processing, vol. 16, No. 2, Feb. 2007, U.S.

Lu et al., Automated Layer Segmentation of Optical Coherence Tomography Images, vol. 57, No. 10, Oct. 2010, U.S.

Bellman, On a Routing Problem, Richard Bellman, vol. XVI, No. 1, The RAND Corporation, pp. 87-90, 1957, U.S.

\* cited by examiner

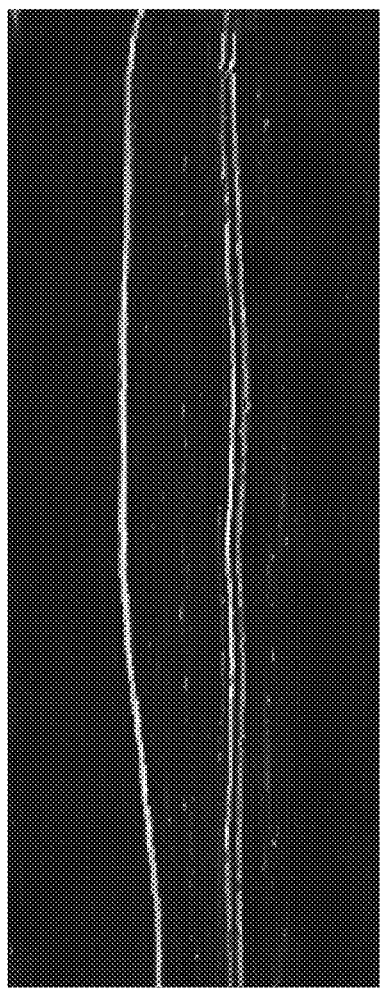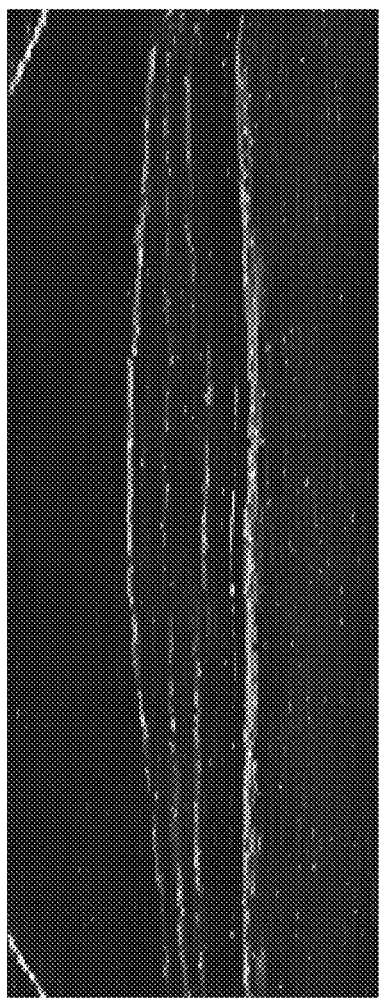

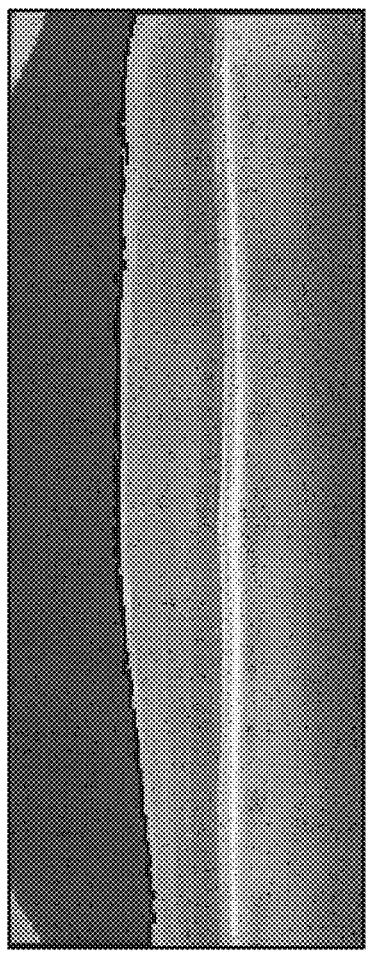 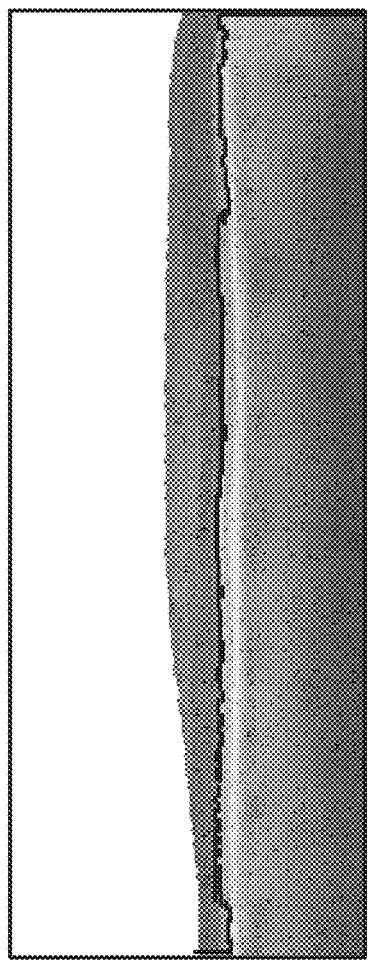
FIG. 8a
FIG. 8b

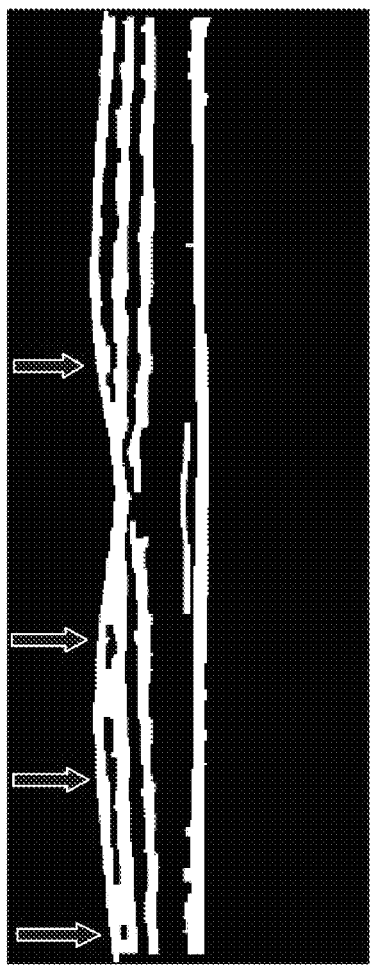
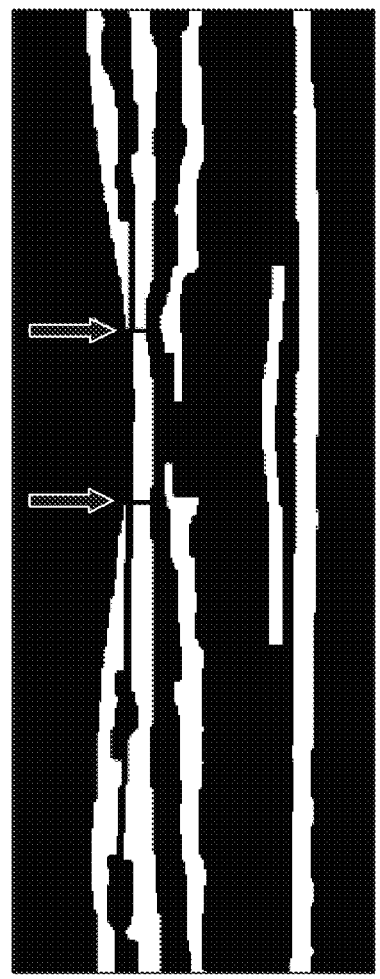
FIG. 10a
FIG. 10b

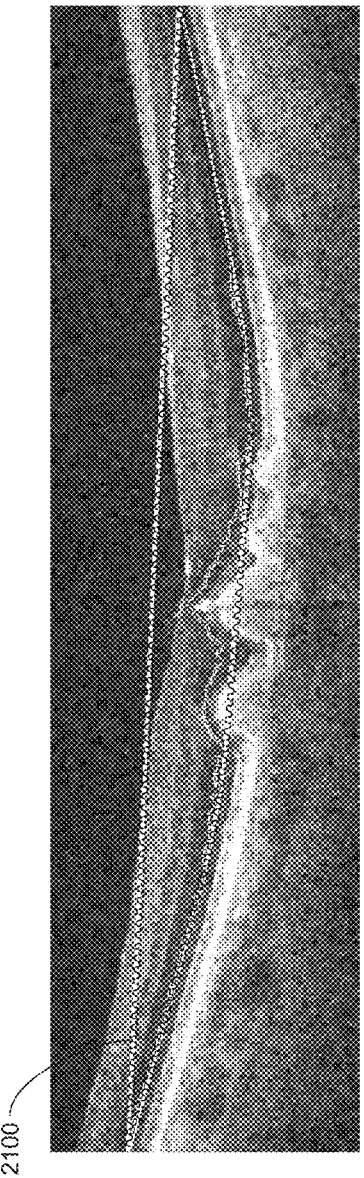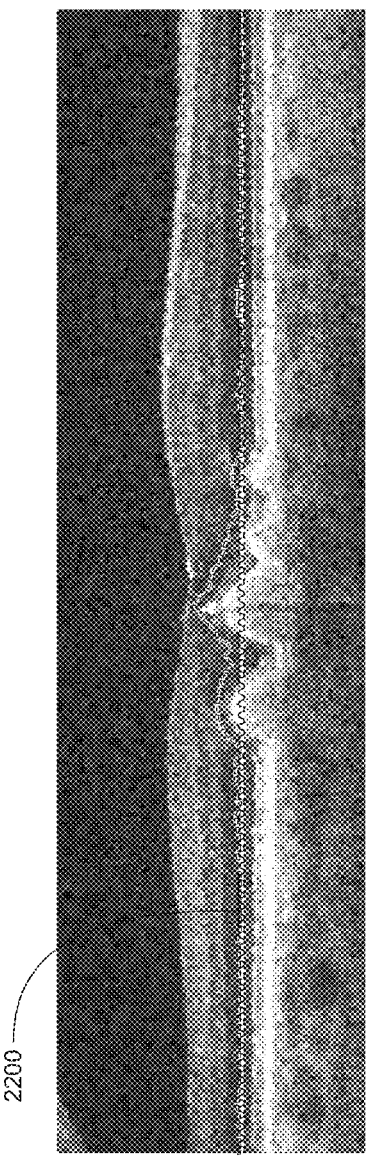

SEGMENTATION AND IDENTIFICATION OF LAYERED STRUCTURES IN IMAGES

CROSS REFERENCE TO RELATED APPLICATIONS

This application is a divisional application of U.S. patent application Ser. No. 13/010,448, filed Jan. 20, 2011, which claims the benefit of U.S. Provisional Patent Application No. 61/296,653, filed Jan. 20, 2010; the disclosures of which are incorporated herein by reference in their entireties.

GOVERNMENT RIGHTS NOTICE

This invention was made with government support under grant number R21 EY019411-A1, awarded by the National Institutes of Health. The government may have certain rights in the invention.

TECHNICAL FIELD

The presently disclosed subject matter relates to imaging and image processing, and more specifically, to systems and methods for segmentation and identification of layered structures in images.

BACKGROUND

Accurate detection of anatomical and pathological structures in Spectral Domain Optical Coherence Tomography (SDOCT) images is critical for the diagnosis and study of ocular diseases. OCT systems are equipped with segmentation software, which have been mainly targeted to measure the nerve fiber layer and the total retinal thicknesses with varying rates of success. As for other ocular features of interest, such as the thickness of the photoreceptor layer, quantitative data is mainly obtained by manual segmentation. Manual segmentation is not only demanding for expert graders, but is also extremely time-consuming for clinical use, or for large scale, multi-center trials. Furthermore, the inherent variability between graders yields subjective results.

Previous reports have addressed different approaches to segmenting retinal layer boundaries with varying levels of success. It is desired to provide improved techniques for segmenting and identifying features in images. More particularly, it is desired to provide systems and methods for segmenting and identifying features of interest in ocular images.

SUMMARY

This Summary is provided to introduce a selection of concepts in a simplified form that are further described below in the Detailed Description of Illustrative Embodiments. This Summary is not intended to identify key features or essential features of the claimed subject matter, nor is it intended to be used to limit the scope of the claimed subject matter.

Disclosed herein are systems and method for segmentation and identification of layered structures in images. According to an aspect, a method may include representing an image as a graph of nodes connected together by edges. For example, the image may be an ocular image showing layered structures of the retina. The method may also include adding, to the graph, nodes adjacent to nodes along first and second sides of the graph. The added nodes may have edge weights less than the nodes along the first and second sides of the graph. Further, the method may include assigning start and end points to any of the added nodes along the first and second sides, respectively. The method may also include graph cutting between the start and end points for identifying a feature in the image.

According to another aspect, a method may include representing an image as a graph of nodes connected together by edges, where the image includes first and second layered features. The method may include graph cutting the graph of nodes to select one of the first and second layered features in the image that is most prominent. Further, the method may include determining intensities of a portion of the image positioned respective of the selected one of the first and second layered features. The method may also include identifying the selected one of the first and second layered feature based on the determined intensities.

According to another aspect, a method may include representing an image as a graph of nodes connected together by edges, where the image includes first and second features. Further, the method may include graph cutting the graph of nodes to select a first set of nodes corresponding to one of the first and second features. The method may also include graph cutting the graph of nodes to select a second set of nodes corresponding to the other of the first and second features. A search associated with graph cutting the graph of nodes to select the second set of nodes is limited to a region of the graph that excludes the first set of nodes.

According to yet another aspect, a method may include representing an image as a graph of nodes connected together by edges, where the image includes first and second layered features. Further, the method may include graph cutting the graph of nodes to select a first set of nodes corresponding to one of the first and second features. The method may also include graph cutting the graph of nodes to select a second set of nodes corresponding to the other of the first and second features, where a search associated with graph cutting the graph of nodes to select the second set of nodes is limited to a region of the graph that excludes the first set of nodes.

According to another aspect, a method may include representing an image as a graph of nodes connected together by edges, where the image includes first and second layered features. Further, the method may include identifying nodes corresponding to first and second layered features. The method may also include determining intensities of pixels of the image. The method may also include determining positions of nodes of the graph corresponding to other layered features based on the determined intensities of the pixels and the determined positions of nodes corresponding to the first and second layered structures.

According to another aspect, a method may include representing an image as a graph of nodes connected together by edges, where the image includes a layered feature and a vessel. The method may also include identifying nodes of the graph corresponding to the vessel by determining a pixel region of the image having intensities with low values with respect to other regions of the image. Further, the method may include setting edge weights of nodes corresponding to the pixel region of the vessel to a predetermined weight value. The method may also include graph cutting the graph of nodes to select the layered feature.

According to yet another aspect, a method may include determining an orientation of a feature in an image. The method may also include representing the image as a graph of nodes connected together by edges. Further, the method may include identifying a set of nodes of the graph based on the determined orientation. The method may also include graph cutting the graph of nodes to select nodes corresponding to the feature. A search associated with the graph cutting excludes the identified set of nodes.

According to another aspect, a method may include representing an image as a graph of nodes connected together by edges, where the image includes first and second layered features. The method may also include determining distances between nodes along first and second graph cuts in the graph, the first and second graph cuts associated with respective search regions. The method may also include determining whether a distance among the distances is less than a threshold. Further, the method may include re-graph cutting one of the first and second graph cuts in response to determining that the distance is less than the threshold. A search region associated with the re-graph cutting is expanded at a region of the nodes corresponding to a location where the distance is less than the threshold.

According to another aspect, a method may include filtering a digitized image including a feature to generate a binary image. The method may include manipulating the binary image using morphological operators to reduce or eliminate noise of artifacts in the binary image. Further, the method may include representing the binary image as a graph of nodes connected together by edges. The method may also include graph cutting the graph of nodes to select nodes corresponding to the feature.

According to another aspect, a method may include identifying nodes corresponding to a layered feature in an image. The method may also include determining convex hull coordinates of the nodes. Further, the method may include moving pixel columns of the image up or down until pixels corresponding to a reference line of the convex hull coordinates extend substantially horizontally for flattening the image.

According to yet another aspect, a method may include identifying a type of a feature in an image. Further, the method may include selecting an image flattening technique based on the identified type. The method may also include applying the image flattening technique to the image for flattening the image.

According to another aspect, a method may include applying an image flattening technique to an image such that pixels in a first region of the image have no data. The method may also include mirroring a second region of pixels of the image onto the first region of the image.

According to another aspect, a method may include representing an image as a graph of nodes connected together by edges. The method may also include biasing weights of the edges based on a portion of anatomy.

According to another aspect, a method may include representing an image as a graph of nodes connected together by edges, where the image includes a feature of anatomy. Further, the method may include biasing weights of the edges by applying an n-lateral weighting scheme based on multiple anatomical and pathological features. The method may also include graph cutting the image to select the feature of the anatomy.

According to yet another aspect, a method may include identifying a type of a feature in an image. The method may also include selecting an image flattening technique based on the identified type. Further, the method may include applying the image flattening technique to the image for flattening the image.

According to another aspect, a method may include applying an image flattening technique to an image such that pixels in a first region of the image have no data. The method may also include mirroring a second region of pixels of the image onto the first region of the image.

According to another aspect, a method may include determining whether a characteristic of pixels corresponding to a feature positioned near an edge of an image meets a predetermined criteria. Further, the method may include unassociating the pixels positioned at the edge from the feature in response to determining that the characteristic of the pixels meets the predetermined criteria.

According to another aspect, a method may include representing an image as a graph of nodes connected together by edges, the image including first and second layered features. The method may also include identifying nodes corresponding to the first layered feature. Further, the method may include defining a search region among the nodes, the search region including a portion of the nodes corresponding to the first layered feature. The method may also include graph cutting the image to select the second layered feature, where the graph cutting is limited to the search region.

According to yet another aspect, a method may include determining an IS-OS boundary estimate based on a search space defined by a location of an OS-RPE boundary. The method may include determining an OS thickness based on the locations of the IS-OS boundary and the OS-RPE boundary. The method may also include assigning the IS-OS boundary as being non-existent in response to determining that the OS thickness is less than a predetermined threshold.

BRIEF DESCRIPTION OF THE DRAWINGS

The foregoing summary, as well as the following detailed description of various embodiments, is better understood when read in conjunction with the appended drawings. For the purposes of illustration, there is shown in the drawings exemplary embodiments; however, the presently disclosed subject matter is not limited to the specific methods and instrumentalities disclosed. In the drawings:

FIGS. 7a and 7b show complementary gradient images used for calculating edge weights in accordance with embodiments of the present disclosure;

FIGS. 8a and 8b show segmentation of FIG. 6b using a Dijkstra technique in accordance with embodiments of the present disclosure;

FIG. 9b is a contrast-enhanced image corresponding to FIG. 9a;

FIG. 10a is a binary mask of the filtered image shown in FIG. 9b;

FIG. 10b is a binary mask with disconnected layers achieved by interpolating the lower boundaries of corresponding holes from FIG. 10a;

FIG. 21 is an image showing an example convex hull encompassing a preliminary RPE line;

FIG. 22 is an image showing a lower portion of the convex hull shown in FIG. 21 being used as the reference line estimate to flatten the retina;

FIG. 23b is an image showing resulting segmentation of the image shown in FIG. 23a;

FIG. 24b is an image showing segmentation of the image of FIG. 24a;

DETAILED DESCRIPTION

The presently disclosed invention is described with specificity to meet statutory requirements. However, the description itself is not intended to limit the scope of this patent. Rather, the inventors have contemplated that the claimed invention might also be embodied in other ways, to include different steps or elements similar to the ones described in this document, in conjunction with other present or future technologies. Moreover, although the term "step" may be used herein to connote different aspects of methods employed, the term should not be interpreted as implying any particular order among or between various steps herein disclosed unless and except when the order of individual steps is explicitly described.

The present subject matter discloses systems and methods for segmenting layered structures in ocular images. The layered structures may be segmented using graph theory and dynamic programming that significantly reduces the processing time required for image segmentation and feature extraction or identification. It should be understood that although the disclosed systems and methods are applied to ocular images, the systems and methods may be applied to any images including features to be segmented or identified. Further, while the disclosed systems and methods are primarily described herein for segmenting retinal layers in SDOCT images, the systems and methods disclosed herein may also be generally applied for segmenting any layered structure in images of any imaging modality.

Figure 1:
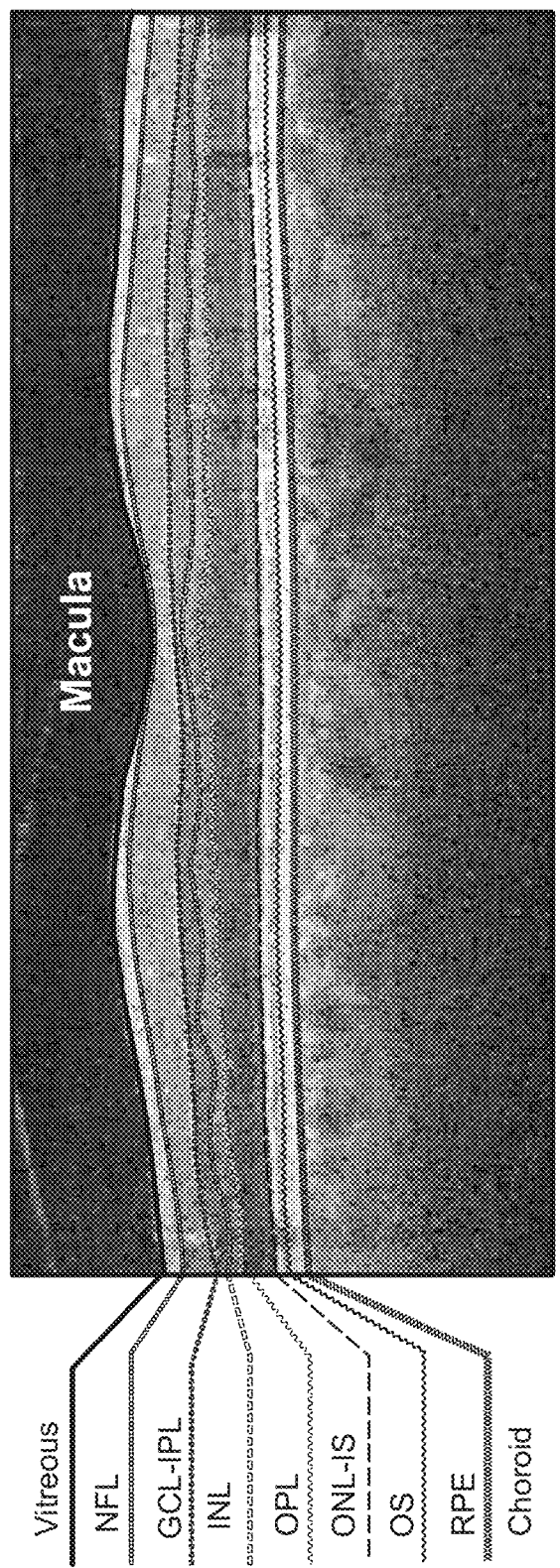
FIG. 1 is a cross-sectional SDOCT image of a retina centered at the macula, annotated with the targeted eight layer boundariesdelineated by a consensus of the expert graders.

FIG. 1 shows a cross-sectional SDOCT image of a retina centered at the macula, annotated with the targeted eight layer boundaries delineated by a consensus of the expert graders. Knowledge of these layer boundary positions allows for retinal layer thickness calculations, which are imperative for the study and detection of ocular diseases. The systems and methods disclosed herein may be used for segmenting the image and identifying boundary types and positions. Particularly, systems and methods disclosed herein may be used for automatically delineating the eight layer boundaries shown in the image.

The systems and methods disclosed herein are beneficial, for example, because they address previous sources of instability including the merging of layers at the fovea, uneven tissue reflectivity, and the presence of pathology. Moreover, the systems and methods disclosed herein overcome prior issues such as vessel hypo-reflectivity, where structural information is lost due to shadowing of the vessels. The presently disclosed systems and methods incorporate a vessel detection method or algorithm for highly accurate segmentation results. Furthermore, the presently disclosed systems and methods provide an adaptable framework for images with pathology such as drusen, as well as pediatric and corneal images, among others. Finally, while many successful segmentation techniques rely on volumetric data to accurately segment anatomic structures, methods disclosed herein are able to accurately segment features of interest in individual B-scans, which is important when volumetric data is not available.

1 Systems and Methods for Layer Segmentation

Figure 2:
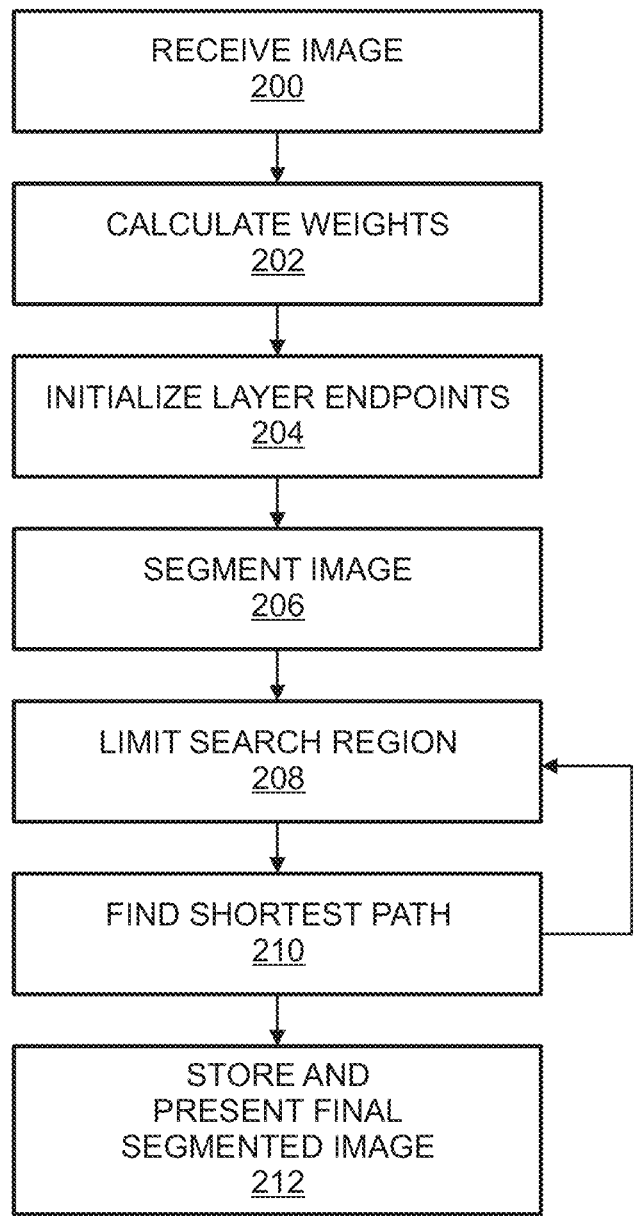
FIG. 2 is a flow chart of an example method for segmenting layer structures in accordance with embodiments of the present disclosure.

This section discloses systems and methods for segmenting layered structures in accordance with embodiments of the present disclosure. For example, FIG. 2 illustrates a flow chart of an example method for segmenting layer structures in accordance with embodiments of the present disclosure. Particularly, FIG. 2 shows various steps in a layer segmentation method, which are described in the following subsections. The method of FIG. 2 may be implemented by any suitable computer, other programmable data processing apparatus, or other devices configured to cause a series of operational steps to be performed on the computer for implementing the method. Similarly, other methods described herein may be implemented by any such devices.

1.1 Graph Representation and Weight Calculation

Referring to FIG. 2, the method includes receiving 200 an image having multiple layered structures. For example, the image may be an SDOCT B-scan showing multiple retinal layered structures. Next, the received image may be represented as a graph of nodes, where each node corresponds to a pixel of the image. In the graph, the links connecting the nodes are referred to herein as "edges." A set of connected edges form a pathway for one to travel across the graph for defining a structured layer. Weights can be calculated 202 and assigned to individual edges to create path preferences. To travel across the graph from a start node to an end node, the preferred path is the route in which the total weight sum is at a minimum. This resulting path is a graph cut which segments one region from another. For example, boundaries between retinal layers correspond to the preferred paths (cuts) on an SDOCT B-scan.

An important aspect of accurately cutting a graph is to assign the appropriate edge weights. Metrics for varying weight values include functions of distances between pixels or differences between intensity values. As long as the feature to be segmented has characteristics unique to its surroundings, low weights can be assigned to the borders of that feature to distinguish it from the rest of the image.

Figure 3:
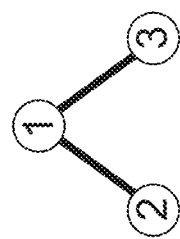
FIG. 3 illustrates a graph with three connected nodes and a corresponding graph weight table in accordance with embodiments of the present disclosure.

Once appropriate weights are assigned to the edges, computationally efficient techniques such as, for example, but not limited to, Dijkstra's algorithm can be used to determine the lowest weighted path of a graph between arbitrary endpoints. Although many of the examples described herein utilize Dijkstra's algorithm, it is emphasized that any other suitable shortest path algorithm which utilize graph theory and adjacency matrices (e.g., utilize the max-flow-min-cut technique) may also be suitable for segmenting or cutting an image in accordance with embodiments of the present disclosure. FIG. 3 illustrates three connected nodes and a corresponding graph weight table in accordance with embodiments of the present disclosure. In an example for finding a minimum weighted path using Dijkstra's algorithm, the weight values must be positive and range from 0 to 1, where an edge weight of zero indicates an unconnected node pair. Referring to FIG. 3, this table of graph weights is defined as the adjacency matrix of a graph, where one axis represents a start node and the other axis indicates an end node. This example illustrates node 1's preference for node 3 due to its lower weight value compared to node 2.

1.2 Endpoint Initialization

While a graph may consist of several layered structures, segmenting a specific layer requires the selection or estimation of the corresponding layer's start and end nodes. For example, referring to FIG. 2, the method includes initializing 204 endpoints. Particularly, the endpoints are automatically initialized. This technique, described in more detail below, serves to bypass the need for manual endpoint selection.

Endpoint initialization in accordance with embodiments of the present disclosure is based on the assumption that the layer to be segmented extends across the entire width of the image. Since Dijkstra's algorithm prefers minimum-weighted paths, an additional column of nodes is added to both sides of the image with arbitrary intensity values and minimal weights $w_{min}$ assigned to edges in the vertical direction. Note that, $w_{min}$ is significantly smaller than any of the non-zero weights in the adjacency matrix of the original graph. In doing so, the nodes in the newly added columns maintain their connectivity, and the graph cut is able to traverse in the vertical direction of these columns with minimal resistance. This allows for the start and end nodes to be assigned arbitrarily in the newly added columns, since the graph cut will move freely along these columns prior to moving across the image in the minimum-weighted path.

Next, the method includes segmenting 206 the image. For example, given a graph with weights associated to edges, segmentation includes cutting the graph by determining a minimum weighted path that connects two endpoints, such as, by use of the Dijkstra algorithm or any other suitable algorithm. Techniques for segmenting an image are described in more detail herein. Once the image is segmented, the two additional columns can be removed, leaving an accurate graph cut without endpoint initialization error.

Figure 4:
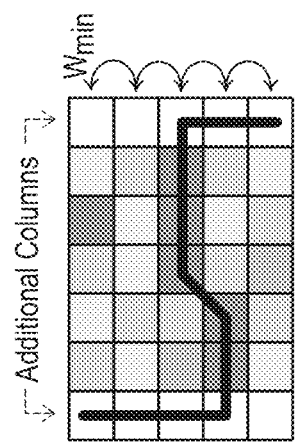
FIG. 4 is an example image segmented using the automatic endpoint initialization technique in accordance with embodiments of the present disclosure.

FIG. 4 is an example image segmented using the automatic endpoint initialization technique in accordance with embodiments of the present disclosure. Two vertical columns are added to either side of the image with arbitrary values (here, the maximum intensity) and minimal vertical edge weights. Furthermore, the start and end points are initialized to the top left and bottom right corners. Edges are assigned weights as a function of pixel intensity, where darker pixels result in a lower weight. Line 400 represents the resulting graph cut using Dijkstra's algorithm. Line points 402 and 404 are the start and end points initialized in accordance with embodiments of the present disclosure. The newly added columns (as indicated in FIG. 4) can then be removed, showing an accurate graph cut despite arbitrary endpoint assignments.

1.3 Search Region Limitation

Oftentimes a feature to be segmented is positioned in an image near extraneous structures with similar characteristics. For example, the inner plexiform layer (IPL) and outer plexiform layer (OPL) regions of the retina are positioned near each other. To prevent the algorithm from accidentally segmenting these structures in place of the target feature, the graph may be limited to a valid search space that excludes any extraneous matter in accordance with embodiments of the present disclosure. In terms of graph theory, this means that the weights of the edges in these invalid regions can be removed prior to cutting the graph for excluding these regions from search. For example, if the inner nuclear layer (INL) region is already accurately segmented, all nodes belonging to the INL or regions above it may be declared as invalid, when searching for the OPL border. Thus, in this example, the nodes corresponding to regions of the INL and the nodes above it may be weighted for excluding these regions from search.

Returning to the example of FIG. 2, the method includes limiting 208 a search region of the image. The search region may be limited after segmentation. For example, nodes corresponding to a previous graph cut and nodes corresponding to other regions respective of the previous graph cut may be excluded in finding a minimum weighted path for another cut. Additional details of limiting a search region according to embodiments of the presently disclosed subject matter are described in more detail herein.

In practice, determining regions that are invalid for search may require particular knowledge about the image and its features. For example, in the case of images of an anatomy, it can be beneficial to have knowledge of features of the anatomy for excluding areas from search where searched for features do not exist. Details of systems and methods for limiting search regions in images, such as retinal SDOCT images, according to embodiments of the present disclosure are discussed in more detail herein below.

1.4 Finding the Minimum-Weighted Path

Given a graph with weights associated to edges, the graph can be cut by determining a minimum weighted path that connects two endpoints. In the example of FIG. 2, the method includes finding 210 a shortest path between the two initialized endpoints. For example, Dijkstra's algorithm may be utilized for finding the minimum or shortest path. Other optimization algorithms which utilize graph theory and adjacency matrices (for example, a max-flow-min-cut technique) may also be used for segmenting the image. Selection of the appropriate algorithm may be determined on a case-by-case basis.

1.5 Feedback and Iteration

Once a first layer boundary is segmented on the image, the process can be repeated recursively by limiting the search space based on the previous graph cut to segment a new layer boundary. The resulting effect is an iterative method in which retinal layer boundaries are segmented by order of prominence. FIG. 2 shows a return of the method to step 208 for search region limiting after finding a shortest path. After the last shortest path is found at step 210, the paths may be labeled, a final segmented image may be stored and presented 212, such as by display.

As described in more detail herein, the presently disclosed systems and methods may handle the rare cases of inaccurate segmentation of one layer such that they do not necessarily affect accurate segmentation of the ensuing layers.

2 Implementation for Segmenting Eight Retinal Layer Boundaries

Figure 5:
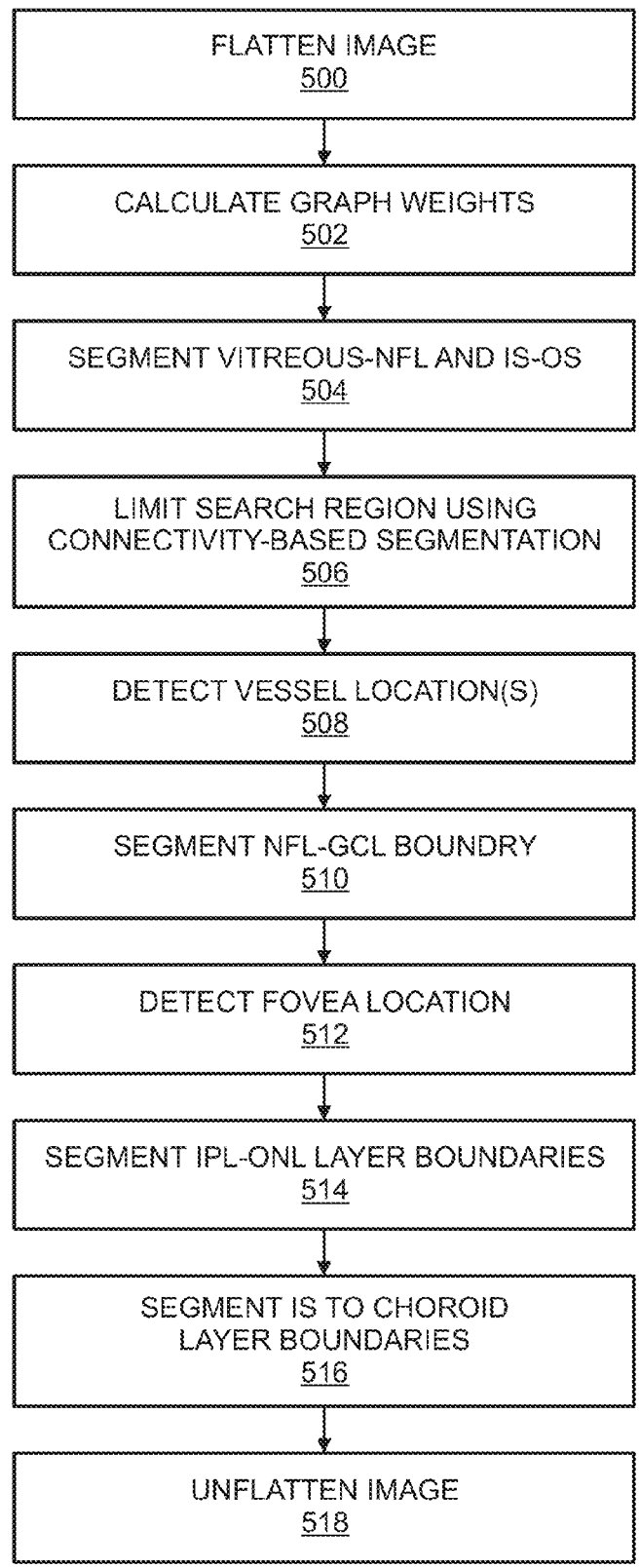
FIG. 5 is a flow chart of an example method for segmenting eight retinal layer boundaries in an SDOCT image according to embodiments of the present disclosure.

This section describes an example method for automatically segments eight retinal layer boundaries in SDOCT images according to embodiments of the present disclosure. In this example, the data to be segmented is assumed to consist of raster scanned images densely sampled in a lateral (B-scan) dimension. Further, in this example, each B-scan is segmented independently from other images within the same volume, and is assumed to be centered at the macula without the optic nerve head present. FIG. 5 illustrates a flow chart of an example method for segmenting eight retinal layer boundaries in an SDOCT image according to embodiments of the present disclosure. The following subsections describe details of the steps of the method of FIG. 5.

2.1 Image Flattening

As discussed in section 1 above, a graph may be segmented by computing the minimum weighted path from a start node to an end node Inherent in this technique is the tendency for the shortest geometric path to be found, since fewer traversed nodes results in a lower total weight. As a result, features with strong curvature or other irregularities, even with relatively strong gradients, may be disadvantaged since their paths do not reflect the shortest geometric distance. As an alternative to a normalized-cut approach, this dilemma may be solved by transforming the image such that the desired path is shortened.

Figure 6A:
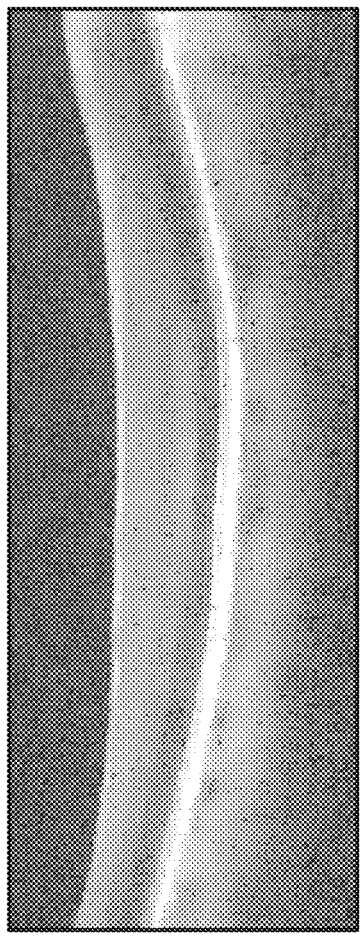
FIGS. 6a and 6b illustrate a retinal SDCOT image with flattening applied in accordance with embodiments of the present disclosure.
Figure 6B:
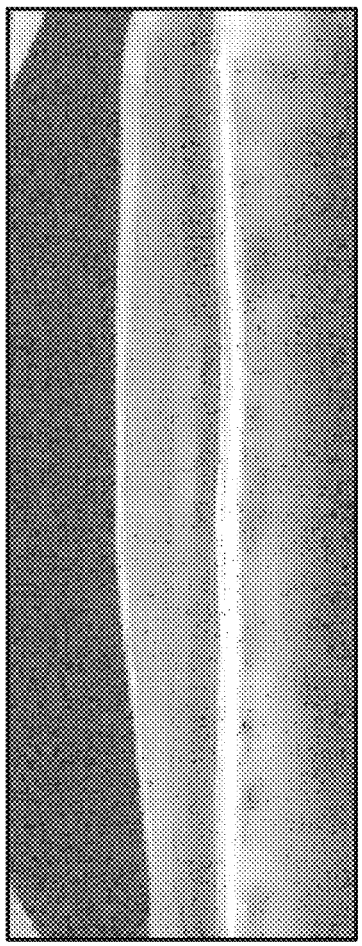

To account for the natural retinal curvature seen in SDOCT images, systems and methods according to embodiments of the present disclosure may flatten the image to avoid inaccurate shortcuts across the layers when segmenting. Referring to FIG. 5, the method includes flattening 500 an image. For example, FIGS. 6a and 6b show retinal flattening of a retinal SDOCT image. Particularly, referring to the figures, FIG. 6a shows the original image, and FIG. 6b shows the flattened version of the original image.

A flattened image may be generated based on a pilot estimate of the retinal pigment epithelium (RPE) layer. In an example, a pilot estimate may be based on prior knowledge that the RPE layer is one of the most hyper-reflective layers within a retinal SDOCT image. Thus, after denoising the SDOCT image with a Gaussian filter, the brightest pixel in each column may be assigned as an estimate of the RPE. Next, an example method may include locating outlier pixels, often associated with the nerve fiber layer (NFL), by searching for discontinuities greater than 50 pixels in the RPE estimate. These outliers are removed from the RPE estimate along with pixels lying in columns that present a significantly lower signal-to-noise ratio (SNR). A second order polynomial may be fitted to the remaining valid RPE points, and each column may be shifted up or down such that the RPE points lie on a flat or horizontal line. Regions of the flattened image that are outside the original field of view are extrapolated from the mirror image of the valid pixels. By this mirroring technique, border artifacts are avoided when later filtering the image. The extrapolated pixels may be excluded from weight calculations, and the resulting image is a smoothly flattened retina image.

2.2 Calculate Graph Weights

The method of FIG. 5 includes calculating 502 graph weights. Graph weights may include two terms representing the geometric distance and intensity difference of the graph nodes. With respect to SDOCT retinal scans, given the relatively high resolution of such scans, most features of interest have a smooth transition between neighboring pixels. Therefore, each node may be associated with only its eight nearest neighbors, sparing the need for including geometric distance weights. All other node pairs may be disconnected, resulting in a sparse adjacency matrix of intensity difference graph weights. For example, an [M×N] sized image has an [MN× MN] sized adjacency matrix with MNC filled entries, where C (here eight) is the number of nearest neighbors. The graph may be defined as undirected, thus halving the size of the adjacency matrix.

In SDOCT images, retinal layers are primarily horizontal structures distinguishable by a change in pixel intensity in the vertical direction. Weights can therefore be calculated solely based on intensity gradients as follows:

$$w_{ab}=2(g_a+g_b)+w_{min}, \text{ where} \tag{1}$$

$w_{ab}$ is the weight assigned to the edge connecting nodes a and b, $g_a$ is the vertical gradient of the image at node a,
$g_b$ is the vertical gradient of the image at node b,
$w_{min}$ is the minimum weight in the graph, a small positive number added for system stabilization.

Equation (1) assigns low weight values to node pairs with large vertical gradients. In this example, $g_a$ and $g_b$ are normalized to values between 0 and 1, and $w_{min}=1\times10^{-5}$. These weights may be further adjusted to account for the directionality of the gradient. To segment the vitreous-NFL layer boundary, for example, it is known that the boundary exhibits a darker layer above a brighter layer. In contrast, the NFL-ganglion cell layer (GCL) layer boundary has a light-to-dark layer change. As a result, edge maps such as [1;−1] and [−1;1] can be utilized when calculating the gradient to extract the appropriate layers. Finally, for automatic endpoint initialization, the end columns may be duplicated and added to either side of the image with vertical edge weights equal to $w_{min}$ and all other weights following Equation (1).

Method and system embodiments disclosed herein for segmenting retinal layers in SDOCT images may yield two undirected adjacency matrices sensitive to either dark-to-light or light-to-dark intensity transitions. For layer boundaries exhibiting a darker layer above a lighter layer such as the vitreous-NFL, INL-OPL, inner segment-outer segment (IS-OS), and OS-RPE boundaries, the dark-to-light adjacency matrix may be utilized. In contrast, for the NFL-GCL, IPL-INL, OPL-PRNL, and RPE-choroid boundaries, which exhibit a lighter layer above a darker layer, the light-to-dark adjacency matrix may be utilized.

FIGS. 7a and 7b show two example, complementary gradient images used for calculating edge weights. FIG. 7a is a dark-to-light gradient image used to generate weights for segmenting the boundary between a darker layer above a lighter layer. FIG. 7b is the corresponding light-to-dark gradient image for boundaries separating a lighter layer above a darker layer.

2.3 Segmenting the Vitreous-NFL and the IS-OS

In accordance with embodiments of the present disclosure, the segmentation of multiple layers is an iterative process, where layer boundaries are graph cut by order of prominence. For example, the method of FIG. 5 includes segmenting 504 the vitreous-NFL and IS-OS. The vitreous-NFL and IS-OS are the two most prominent layer boundaries in an SDOCT retinal image due to their high contrast in pixel intensity. Dijkstra's method and the dark-to-light graph weights may be utilized to find the lowest-weighted path initialized at the upper left and the bottom right pixels of the image. The resulting graph cut is either the vitreous-NFL or the IS-OS.

The vitreous-NFL is the topmost layer of the retina on a B-scan with little hyper-reflectivity above it, unlike the IS-OS. The method may include inspecting the region directly above the cut for bright layers in order to determine which layer boundary was segmented. If there is no hyper-reflectivity present in the region, the method may determine that the segmented layer is the vitreous-NFL. Otherwise, the method may infer that the IS-OS is detected. In order to determine the presence or absence of hyper-reflectivity, the image may be first low-pass filtered with a Gaussian kernel and thresholded using a suitable technique, such as Otsu's method, to generate a binary mask. This step isolates the NFL-OPL and IS-RPE complexes. The fraction of bright pixels in the region above the cut may then be calculated for the binary image. If the fraction exceeds 0.025, the method may conclude that the segmented layer boundary is the IS-OS due to the presence of the NFL-OPL complex. Otherwise, the method may conclude that the vitreous-NFL layer boundary was segmented.

In accordance with embodiments of the present disclosure, a limited search space technique as generally described in Section 1.3 may be applied. For example, if the IS-OS layer boundary was first segmented, the search space may be limited to a region 20 pixels above the segmented line so the vitreous-NFL can be segmented next. More, generally the search space may be limited to any suitable portion of the image respective to the position of the IS-OS layer boundary. In contrast, if the vitreous-NFL was segmented first, then the search space may be limited to a region 40 pixels below it to segment the IS-OS. As a result, the two most prominent layer boundaries in the image are segmented.

FIGS. 8a and 8b show segmentation of FIG. 6b using a Dijkstra technique in accordance with embodiments of the present disclosure. Particularly, FIG. 8a shows an SDOCT B-scan, where the vitreous-NFL is first segmented as indicated by the dark solid line, given a search space of the entire image. The search region is then limited to the space shown in FIG. 8b, resulting in the segmented IS-OS line as indicated by the dark solid line. This example also shows the result of the automatic endpoint initialization described in Section 2.2. Lastly, it is noted that the pilot IS-OS layer detected at this stage may be inaccurate due to IS-OS and RPE layer confusion. Such errors may be corrected in accordance with the techniques described in Section 2.8.

2.4 Search Region Limitation Using Connectivity-Based Segmentation

While the vitreous-NFL and IS-OS may be easily identifiable due to their prominent hyper-reflectivity, the remaining layer boundaries are not as distinct. To accurately segment these remaining layers, a method according to embodiments of the present disclosure defines a valid and narrow search region that isolates the layer boundaries of interest. For example, the method of FIG. 5 includes limiting 506 a search region using connectivity-based segmentation. This technique for limiting the search region may be implemented in two steps. In the first step, a pilot estimate of pixel clusters is developed that corresponds to the hyper-reflective layer regions using a column-wise intensity profiling technique. In the second step, which may be referred to as the connectivity-based step, clusters associated with a particular layer may be connected and modified. The resulting layer estimations may be used to limit search regions in Sections 2.6 to 2.8, in which three of the estimated layer boundaries are considered at a time. The top and bottom of these layers may be used as the search space area for identifying the graph cut that represents the middle layer.

Figure 9A:
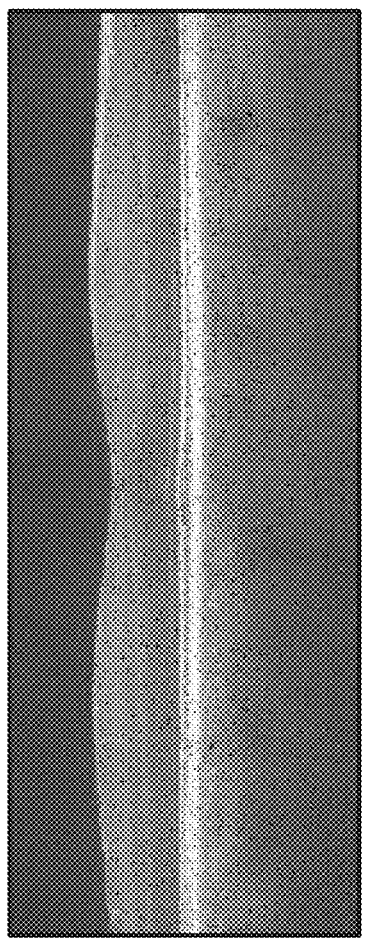
FIG. 9a is a flattened retinal SDOCT image.
Figure 9B:
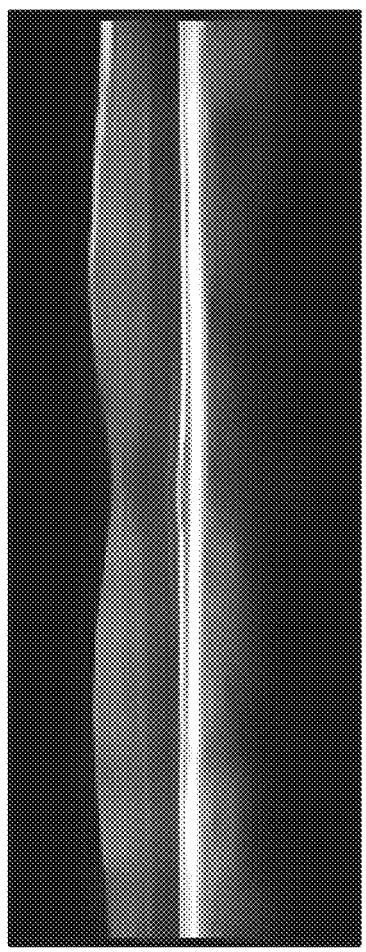

Example two column-wise intensity profiling and connectivity-based segmentation steps include first enhancing the contrast between the light and dark layers. To achieve this, the image may be coarsely denoised with a rectangular averaging filter of size 3×19 pixels or any suitable size of pixels. Next, this image may be threshold by setting the values of pixels that are smaller than the median of their corresponding column to zero. An example contrast-enhanced image is shown in FIG. 9b, which corresponds to FIG. 9a, a flattened retinal SDOCT image.

Next, a binary mask may be generated to isolate the hyper-reflective retinal layers. For example, the 1-D, column-wise, second-order derivative of the contrast-enhanced image may be taken to boost layer boundaries. Next, a pilot binary mask may be created by thresholding the edge-enhanced image at zero. Then, to remove outliers in each column, all non-zero clusters may be set to less than 5 pixels tall to zero, and the remaining clusters may be joined that are closer than 3 pixels from each other. The resulting mask corresponds to the hyper-reflective layers in the retina (i.e. NFL, IPL, OPL, IS-OS, RPE). A horizontal 1-D closing operation with a kernel of 10 pixels in size may be performed on the image as a whole to close gaps, and any clusters less than 500 pixels in size may be removed. The result is a coarse binary mask of the hyper-reflective retinal layers, as shown in the example of FIG. 10a.

The layers in some columns of the coarse binary mask may be blended together, as seen in the top layers of FIG. 10a, for example. These merged hyper-reflective layers may be distinguished by interpolating the approximate location from neighboring columns in which they are detached. This may be accomplished by first detecting hyper-reflective pixel clusters with holes corresponding to a partially detected middle hypo-reflective layer. For example, the merged NFL and IPL clusters and the holes corresponding to the GCL layer in FIG. 10a are noted. The merged layers may be cut by interpolating the lower boundaries of corresponding holes, separating all layers as shown FIG. 10b. It is noted that the interpolating line may not break all merged layers into two clusters, as is the case in the foveal region of FIG. 10b. These areas are separated from the original cluster with vertical lines.

Next, search region limiting may include examining each column in the original binary mask (for example, the binary mask shown in FIG. 10a) and tentatively assigning each cluster of pixels within the column to a particular anatomical layer. The available choices for hyper-reflective layers are the NFL, IPL, OPL, IS-OS, RPE, or "no assignment" in the case that the rules fail to reach a reasonably certain assignment. To do this, the number of clusters may be counted for each column. For columns with five clusters, retinal layer assignments can be straightforward since there is a one-to-one correspondence with the targeted layers. To determine the missing layers in columns with fewer than five clusters, knowledge of the layer order and approximate layer distances may be used advantageously. For example, it may be assumed that the OS-RPE is at least 30 pixels below the vitreous-NFL, and the distance between the RPE and IS-OS layers is less than 10 pixels. The end result is the tentatively-assigned retinal layers shown in the example of FIG. 11a, which illustrates column-wise retinal layer assignments of the mask shown in FIG. 10a. The conflicts in the top three layer assignments should be noted.

Figure 11A:
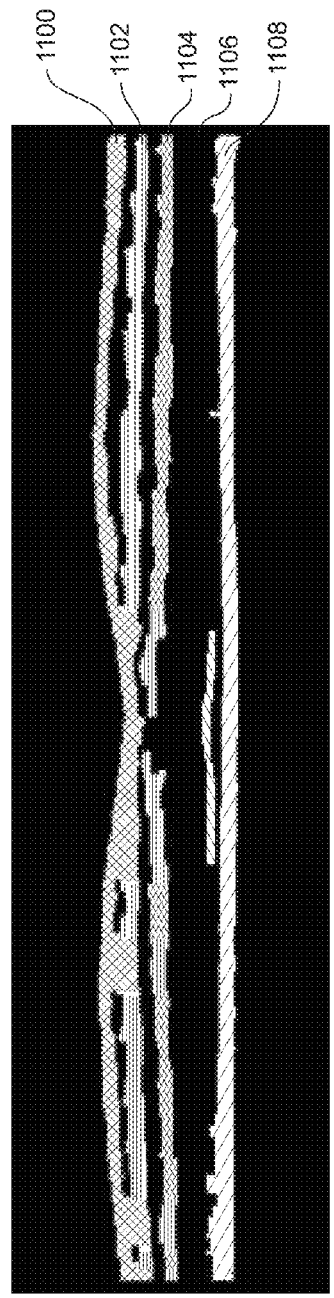
FIGS. 11a and 11b are images showing retinal layer assignments.
Figure 11B:
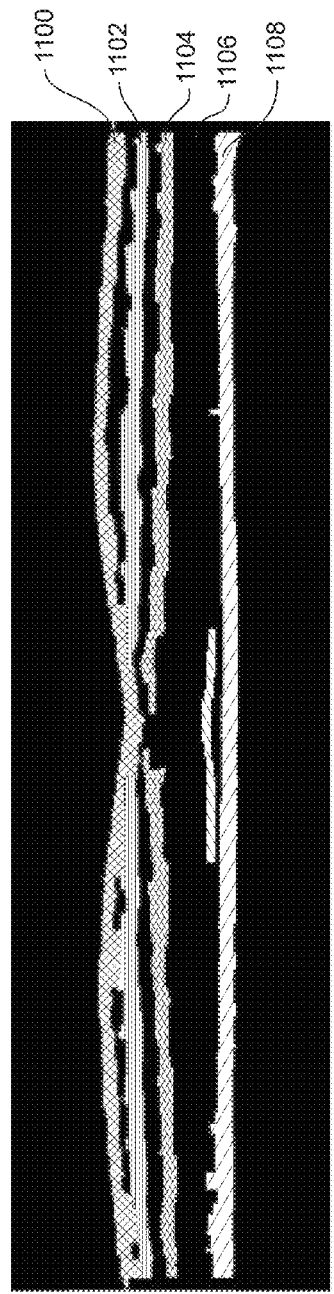

To correct possible conflicts in the column-wise layer assignments where a spatially connected group of pixels may have tentative assignments to different retinal layers such as shown, for example, in FIG. 11a, a voting scheme may be utilized. In the voting scheme, all connected pixels may be reassigned from a 2-D binary cluster to a single retinal layer based on the majority tentative assignment of the pixels in that cluster. The result from this cluster-based refinement method is shown in FIG. 11b, which illustrates the cluster layer assignments of the mask shown in FIG. 10b. In FIGS. 11a and 11b, retinal assignments are as follows: line 1100 is NFL; line 1102 is IPL; line 1104 is OPL; line 1106 is IS-OS; and line 1108 is RPE.

Figure 12:
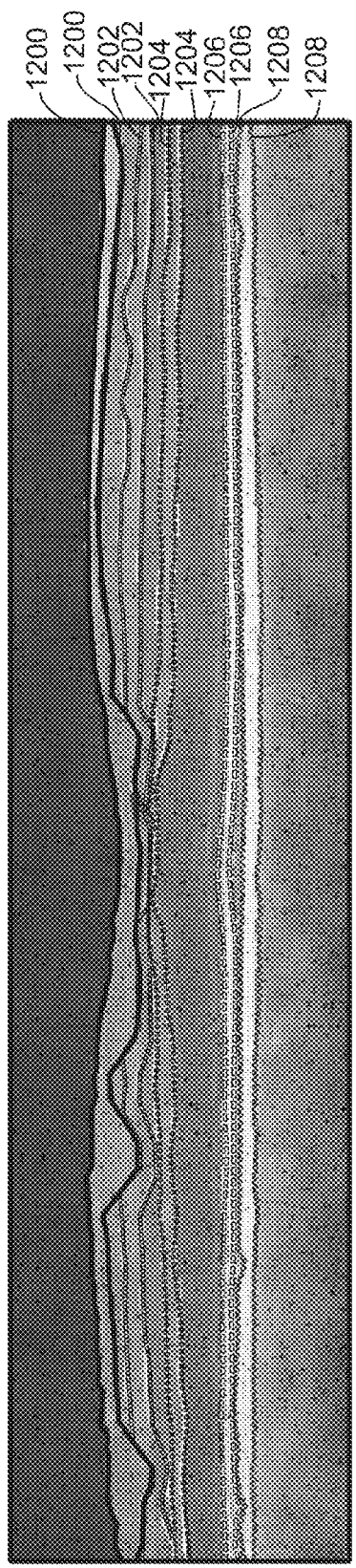
FIG. 12 is an image showing connectivity-based segmentation of retinal layers using layer assignments from FIG. 11b.

The boundaries of the NFL, IPL, and OPL may be determined by finding the top and bottom edges of the assigned pixel clusters. An example is shown in FIG. 11b. The boundaries of the IS-OS and RPE may be found by first distinguishing the two layers from each other. The brightest pixels in the filtered image (for example, the filtered image of FIG. 9b) that are (a) given the IS-OS/RPE layer assignment in the original mask (for example, FIG. 10a), and (b) furthest from the top of the image, may be assigned as the center of the RPE. This center RPE line may then be smoothed with a median filter. The RPE edges may be located by performing a focused search for large changes in gradient near the center RPE line on the filtered image (for example, the filtered image shown in FIG. 9b). The same can be done to find the IS-OS edges by searching just above the RPE layer, resulting in the estimated retinal layers shown in FIG. 12. Referring to FIG. 12, retinal assignments are as follows: lines 1200 are NFL; lines 1202 are IPL; line 1204 is OPL; line 1206 is IS-OS; and line 1208 is RPE. Because these layer estimations may still contain errors, they may be refined, as described in subsequent subsections, using, for example, Dijkstra's method, with adjacent layer estimations as search region boundaries.

2.5 Vessel Detection

Figure 13A:
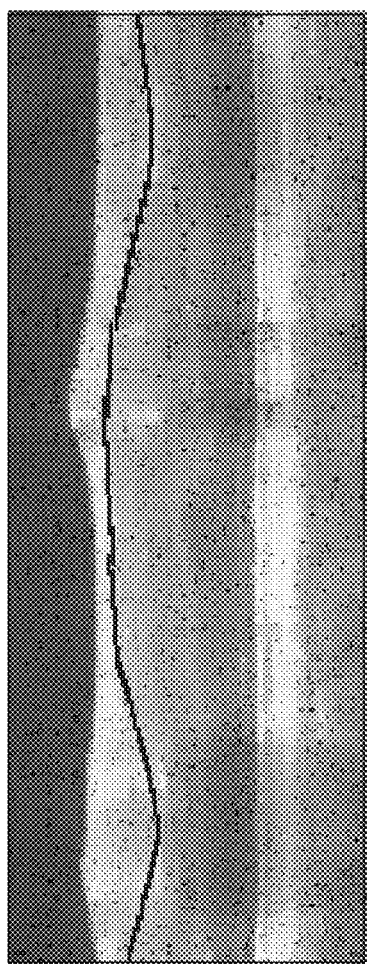
FIG. 13a is an image showing NFL-GCL without vessel detection.

Retinal SDOCT images with prominent vessels can pose a challenge when segmenting the NFL-GCL boundary, because they result in hyper-reflective bulges in the NFL layer as shown in the example image shown in FIG. 13a, which illustrates an image showing NFL-GCL (indicated by the solid dark line) without vessel detection. In an example, retinal blood vessels may be located through iterative polynomial smoothing. To address this problem, system and method embodiments are disclosed herein for detecting vessels, particularly on individual B-scans to make Dijkstra's algorithm indifferent to bulges in the NFL layer. The method of FIG. 5 includes detecting 508 one or more vessel locations in the image.

In a first example step of detecting vessel locations, the RPE-choroid layer boundary may be tentatively segmented, where a pilot IS-OS is used to limit the search region. Then, a Gaussian filter may be applied to the image, and columns ranging from the RPE-choroid to 15 pixels above may be summed. Columns exhibiting low sum values, corresponding to the dark areas from vessel shadowing, may be defined as the vessel regions.

Figure 13B:
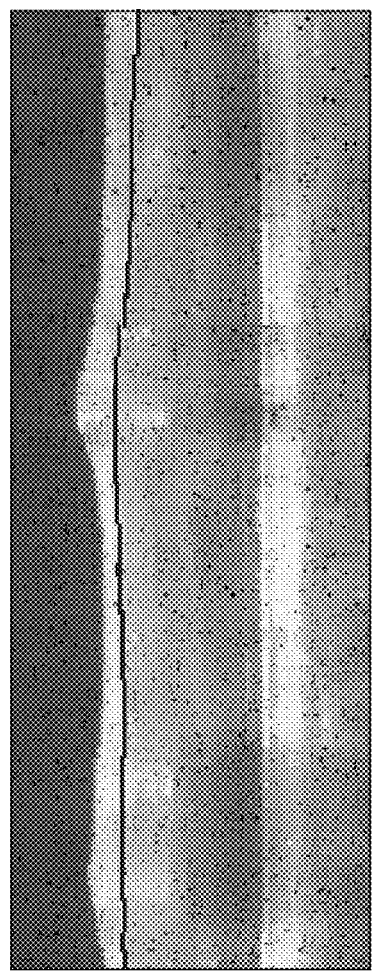
FIG. 13b is an image showing NFL-GCL with vessel detection applied according to embodiments of the present disclosure.

In a second example step for detecting vessel locations, edge weights in the vessel regions may be set to $w_{min}$ prior to segmenting the NFL-GCL. Upon updating the graph weights, the NFL-GCL cut may be indifferent to these vessel regions. For example, FIG. 13b is an image showing NFL-GCL with vessel detection applied according to embodiments of the present disclosure. The example of FIG. 13b demonstrates the effectiveness of the vessel correction algorithm in improving the accuracy of the NFL-GCL boundary detection, which is described in Section 2.6.

2.6 Segmenting the NFL-GCL

The method of FIG. 5 includes segmenting 510 the NFL-GCL boundary. For example, after incorporating minimum weights in the vessel regions and estimating the layer boundaries using connectivity-based segmentation, a pilot estimate of the NFL-GCL layer boundary may be formed using Dijkstra's algorithm, or another suitable algorithm, and the updated light-to-dark graph weights. The search region may be limited using the vitreous-NFL from Section 2.3 and the estimated IPL-INL from Section 2.4 prior to cutting. Errors may arise, however, due to the similar light-to-dark gradient characteristics of the NFL-GCL and IPL-INL layer boundaries. Moreover, the NFL layer is thicker on the nasal side of the fovea that is closer to the optic nerve head, necessitating an asymmetric, larger search region.

Segmentation of the NFL-GCL boundary may include a technique to account for NFL-GCL/IPL-INL confusion. In this technique, the temporal side may be predetermined based on knowledge of the scan direction (horizontal/vertical) and which eye (left/right) was imaged. For example, horizontal scans of the left eye exhibit layer thinning on the right side of the fovea, whereas vertical scans of the left eye show layer thinning on both sides of the fovea.

Using the vitreous-NFL from Section 2.3 and the preliminary NFL-GCL cut, the NFL thickness may be estimated. Moving across the image from the thicker to the thinner side of the layer, the first instance may be found where the thickness drops below a threshold of 6 pixels and it may be marked as the divide between the thick and thin sides. The search region on the thinner NFL side may be limited to 10 pixels below the vitreous-NFL, and the search region on the thicker side may be expanded from 5 pixels below the vitreous-NFL to 5 pixels below the preliminary NFL-GCL cut.

Figure 14A:
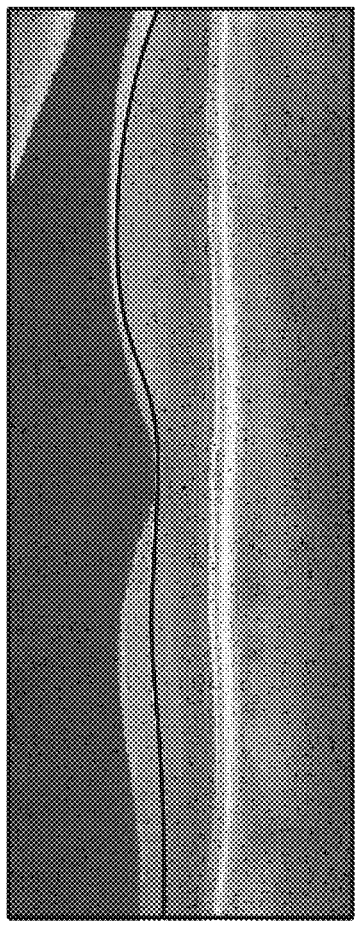
FIG. 14a is an image showing NFL-GCL before correction.
Figure 14B:
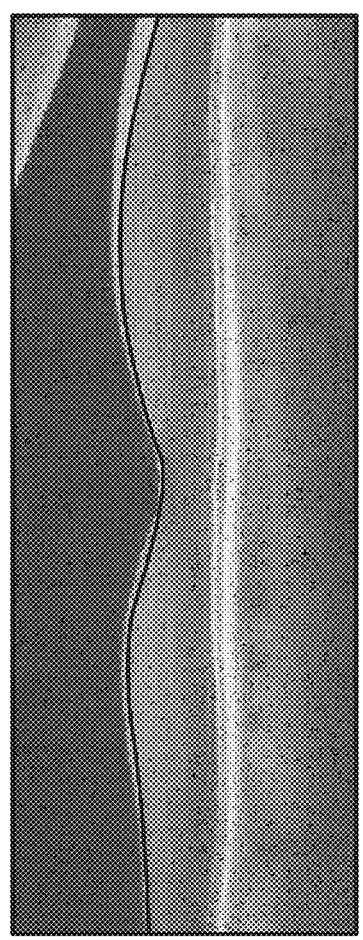
FIG. 14b is an image showing NFL-GCL after correction.

FIGS. 14a and 14b show an example image of resulting NFL-GCL segmentation (indicated by the solid dark line) before and after correcting the layer boundary. Particularly, FIG. 14a shows a segmented image before correction, and FIG. 14b shows a segmented after correction

2.7 Detecting the Fovea and Segmenting the IPL to ONL Layer Boundaries

Figure 15A:
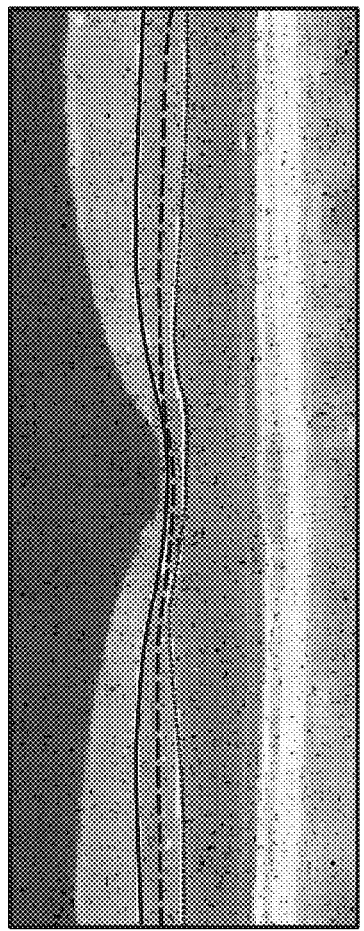
FIG. 15a is an image showing segmentation before fovea correction.

The method of FIG. 5 includes detecting 512 the fovea location and segmenting 514 the IPL-outer nuclear layer (ONL) boundaries. It is important to detect whether the image contains the fovea, since layers tend to merge together and become increasingly indistinguishable near the fovea. Due to inaccuracies in estimating layer boundaries, errors similar to those shown in the example of FIG. 15a often appear in the pilot segmentations for B-scans containing the fovea. To address such problems, a pilot estimate of the IPL-INL, INL-OPL, and OPL-ONL layer boundaries may be performed using an appropriate weighting matrix (light-to-dark or dark-to-light) and a suitable algorithm, such as Dijkstra's algorithm. The search regions may be limited using the previously segmented lines and the estimated layer boundaries from Section 2.4. For example, the IPL-INL search region may be limited to 3 pixels below the NFL-GCL, and above the estimated IPL-INL or INL-OPL boundaries, whichever is higher.

In a next example step, the presence and location of the fovea may be estimated by calculating the NFL, GCL-IPL, INL, and OPL layer thicknesses from the tentatively segmented layers. Columns with a mean layer thickness of less than 5 pixels may be assigned as the foveal region. Since this region may not necessarily be centered at the fovea, the center may be located by calculating the vitreous-NFL to IS-OS thickness, where the column containing the minimum thickness is located and expanded by 20 pixels on either side. If this region coincides with the foveal region detected prior, then it may be included as a part of the fovea.

Figure 15B:
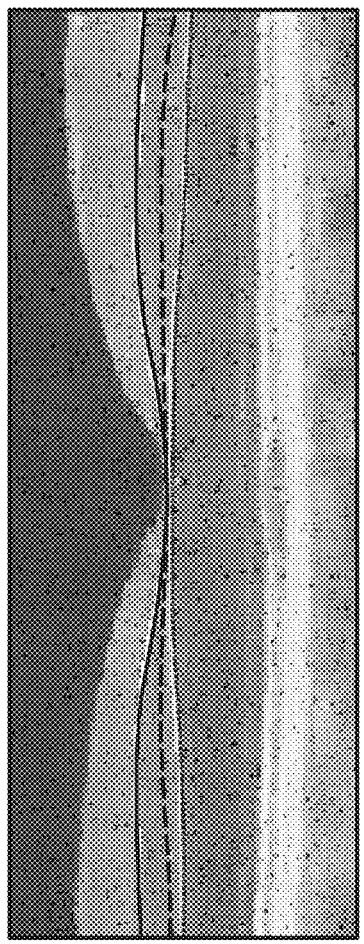
FIG. 15b is an image showing segmentation after fovea correction.

After locating the fovea, more accurate search regions may be defined to account for foveal layer merging. This may be accomplished by maintaining the position of the lower boundary of the search space, however expanding the top boundary of the search space upward to reach the vitreous-NFL when re-segmenting the IPL-INL, INL-OPL, and OPL-ONL. An example of the resulting segmentations that are more accurate are shown in FIG. 15b, which shows the segmented image after correction of the segmented image shown in FIG. 15a.

2.8 Segmenting the IS to Choroid Layer Boundaries

The method of FIG. 5 includes segmenting 516 the IS to choroid layer boundaries. The remaining lower boundaries (IS-OS, OS-RPE, and RPE-choroid) may be segmented exploiting the previously estimated layer boundaries, the connectivity-based search regions, and Dijkstra's algorithm or any other suitable algorithm. In particular, the IS-OS estimate from Section 2.3 may be improved upon to remove any possible IS-OS/OS-RPE confusion. In accordance with embodiments of the present disclosure, the IS-OS may be re-segmented with a modified search region ranging from 4 pixels below the segmented OPL-ONL line to 2 pixels above the estimated OS-RPE from Section 2.4.

After segmenting all layer boundaries, the method of FIG. 5 includes unflattening 518 the image. For example, the image may be unflattened by shifting the pixels up or down in the direction opposite to image flattening, thereby restoring the original curvature. Thus, this example may be used to segment 8 retinal layer boundaries on a given SDOCT image.

3 Application to Images with Age-Related Macular Degeneration (AMD) Pathology Age-related macular degeneration (AMD) is a leading cause of irreversible blindness in Americans over 60 years of age. SDOCT imaging systems provide a non-invasive, cross-sectional view of the retina to aid in the research and diagnosis of AMD. Systems and methods in accordance with embodiments of the present disclosure may be utilized for automatically segmenting retinal layers in SDOCT images with AMD pathology. Further, system and method embodiments disclosed herein may identify drusen and geographic atrophy (GA). Embodiments of the presently disclosed subject matter can be beneficial for precise measurement of drusen, which may be critical for assessment of disease load and then of the effect of treatment. Thus, the systems and methods disclosed herein can be critical for clinical care since the drusen size (volume) is likely to determine a patient's risk of progression or of vision loss. This may also be important for testing of future therapy to prevent drusen formation or clear drusen.

In accordance with embodiments of the present disclosure, systems and methods are disclosed for segmentation of neurosensory retina in SDOCT images with non-neovascular AMD. As described in further detail herein below, graph theory and dynamic programming techniques are utilized to focus on, for example, the segmentation of three retinal boundaries in SDOCT images with AMD pathology: the vitreous-NFL boundary and the two boundaries isolating the RPE and drusen complex. Further, as described herein below, a validation study was conducted to verify that the segmentation results were accurate and reliable. Embodiments of the presently disclosed subject matter can be beneficial for monitoring the effect of therapy. As can be understood, for any disease process, a more precise measure of the size and extent of the disease may improve ability to monitor for change in the disease and identify beneficial or detrimental change.

Figure 18:
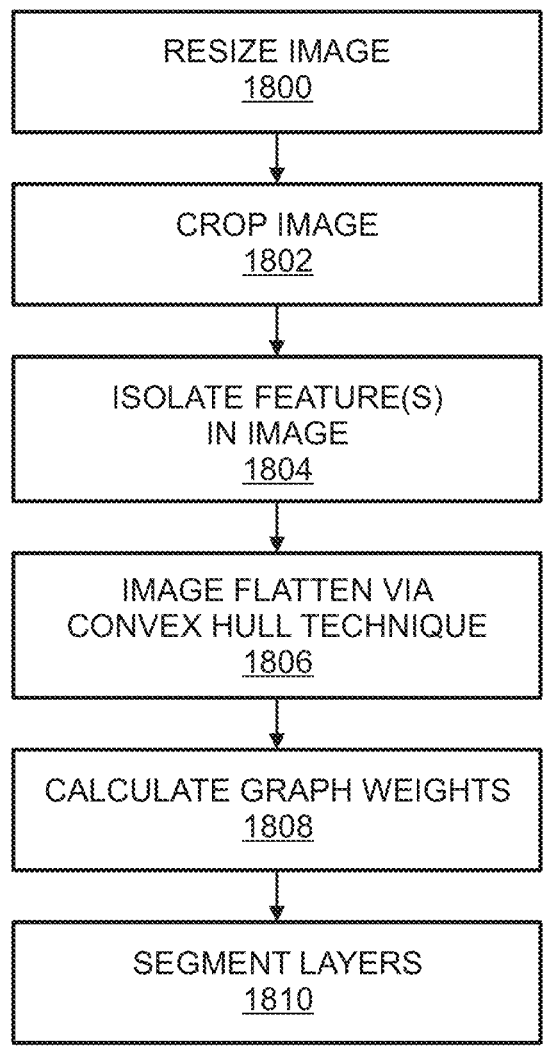
FIG. 18 is a flow chart of an example method for segmenting retinal layers in AMD eyes in accordance with embodiments of the present disclosure.

FIG. 18 illustrates a flow chart of an example method for segmenting retinal layers in AMD eyes in accordance with embodiments of the present disclosure. Details of the method of FIG. 18 are disclosed herein below. The method of FIG. 18 may be implemented by any suitable computer, other programmable data processing apparatus, or other devices configured to cause a series of operational steps to be performed on the computer for implementing the method. Similarly, other methods described herein may be implemented by any such devices.

3.1 Image Resizing

The method of FIG. 18 includes resizing 1800 an image. For example, the image may be an SDOCT image having AMD pathology. Image resizing may be beneficial to reduce the computational cost associated with the creation and storage of an adjacency matrix. To decrease the overall computation time, the amount of redundant information may be reduced by downsampling the image. It is noted that slowly varying structures, such as the retinal layers in normal subjects, can be heavily downsampled while still achieving accurate results. For structures with fast local variation in shape, such as the retinal pigment epithelium (RPE) of AMD patients with drusen, downsampling may be limited. That is, by multi-scale decomposition of the image (wavelet transform), an optimal approach for image analysis may be obtained. Prior information about the size of the structure to be segmented can be utilized to determine an optimal downsampling rate. It is noted that downsampling can be anisotropic for images which have finer detail in one direction as compared to the other (i.e., retinal OCT images which usually have higher spatial frequencies perpendicular to the retinal layers than parallel to them).

Another benefit of image resizing is the capability to accurately segment images of varying resolutions. Prior information about the structure size (e.g., retinal layer thickness) may utilized to distinguish between different structures. This information may be utilized in the form of pixels (e.g, layer A is 4 pixels thick, and layer B is 10 pixels thick). Since images may be captured using different sampling frequencies, the resulting pixel thickness of the same structure may be different. By resizing each image so that the structure of interest is a standard size (e.g., always a certain pixel value in thickness), the method may segment images of varying resolution.

3.2 Image Cropping

The method of FIG. 18 include cropping 1802 the image. If the structure to segment is contained in only a portion of the image, the image can be cropped to reduce the adjacency matrix size, thus reducing computation time. Furthermore, if any image artifacts are present outside of the structure, cropping these artifacts out of the image can reduce any later confusion between the desired structure and any artifacts present in subsequent processing. It is noted that artifacts embedded within the desired structure may alternatively be circumvented using a different technique as described herein below.

For retinal images, there are often artifacts that appear in the form of white horizontal bands. Unlike retinal structures, the variance of these artifacts is low across the width of the image. Image rows with only noise also exhibit a low variance. By isolating and removing image rows with an extremely low variance with respect to rows containing signal, the artifacts and portions of the image with no signal can be cropped out.

3.3 Feature or Structure Isolation via Binary Mask

The method of FIG. 18 includes isolating 1800 features in the image. Often with complex structures and morphologies, extraneous features can be mistaken for the feature or structure to be segmented. It is therefore important to isolate the desired feature as much as possible prior to segmentation using a technique referred to herein as search region limitation. In search region limitation, all edges outside of the desired search region may be excluded when finding the shortest path, resulting in a pathway that fully traverses across the region with edges intact.

Figure 19:
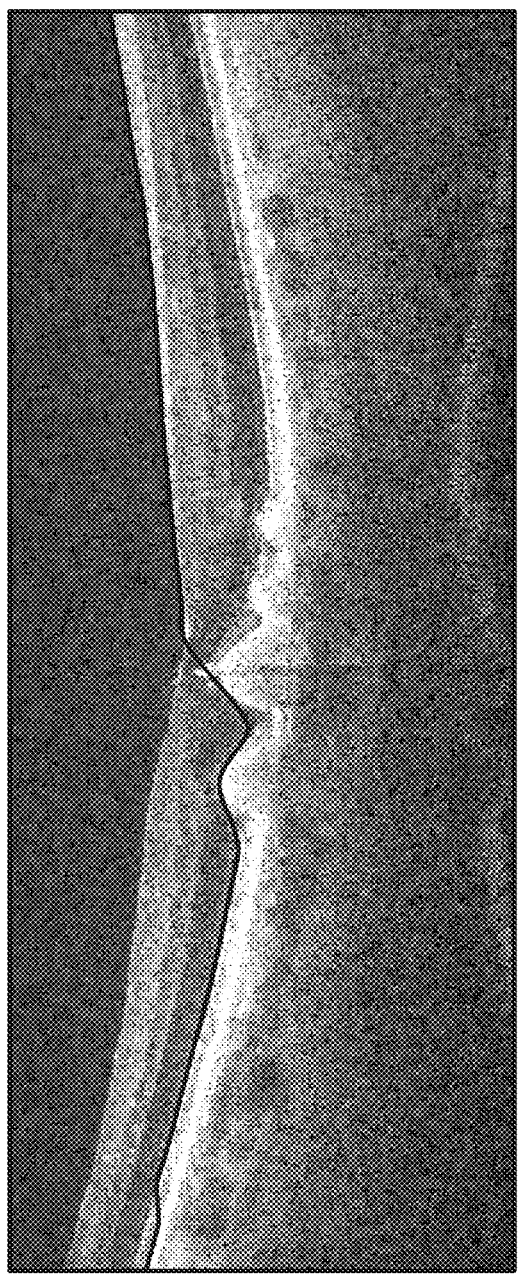
FIG. 19 is an image showing a graph cut resulting from IS-OS and vitreous-NFL structure confusion.

In an example, for retinal images with pathology such as AMD, the accumulation of extracellular material, or drusen, raises the retinal RPE layer towards the NFL, causing the two layers to nearly merge. If the search region is not limited prior to segmenting, the vitreous-NFL and IS-OS or RPE layers can be mistaken for each other since they can have similar characteristics, as seen in the image shown in FIG. 19, which illustrates an image including an erroneous graph cut (indicated by the dark solid line) produced due to IS-OS and vitreous-NFL structure confusion.

Figure 20:
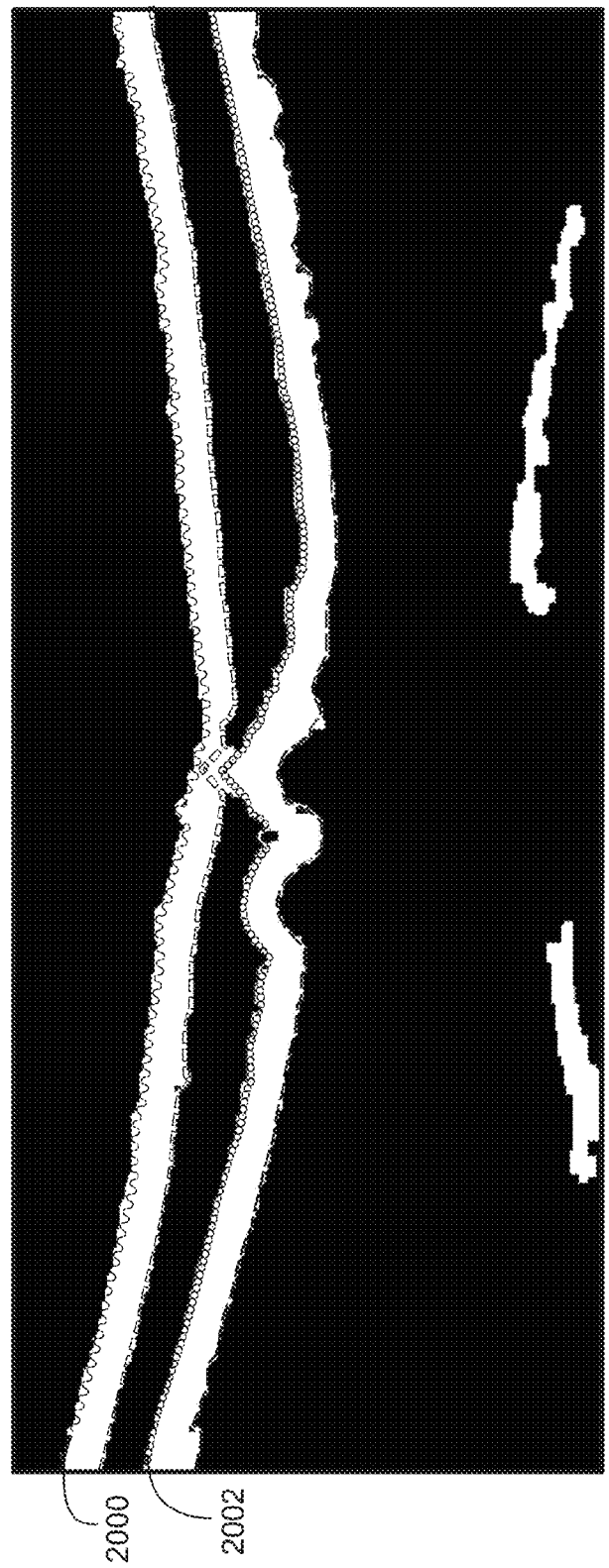
FIG. 20 is an image indicating binary mask isolation of the hyper-reflective NFL-OPL and IS-RPE complexes.

To isolate the NFL from the IS-RPE complex, the image can be separated into the NFL-OPL complex and the IS-RPE complex. To accomplish this, the image can be filtered to reduce noise and thresholded to generate a binary mask isolating the hyper-reflective NFL-OPL and IS-RPE complexes. For example, FIG. 20 is an image indicating binary mask isolation of the hyper-reflective NFL-OPL and IS-RPE complexes. The boundaries of these complexes may be determined using a graph theory and dynamic segmentation technique according to embodiments of the presently disclosed subject matter. Morphological functions such as closing and opening operations can be used to refine the mask, and connected component functions can be utilized to remove small, undesired clusters originating from the vitreous or choroid regions.

Example steps taken for generating a binary mask in accordance with embodiments of the presently disclosed subject matter includes smoothing the image with a Gaussian filter. Next edges may be extracted using a [−1;1] edge filter (notation corresponding to MATLAB's definition of vectors). An example step includes setting all values below a threshold to zero, and all values above the threshold to 1. Next, an open morphological function with a rectangular structuring element may be used to open any gaps in the clusters. Next, all connected clusters may be located, and clusters that are smaller than a predetermined size may be removed. Another example step includes using the close morphological function with the rectangular structuring element to close any gaps in the clusters.

Once the mask is generated, the borders of the two white bands (corresponding to the two NFL-OPL and IS-RPE complexes) are found so the regions can be isolated. Due to the large difference in image quality and pathology present in the various images, however, the resulting mask will often still contain undesired clusters and the two hyper-reflective bands can either be merged or each appear in disjoint segments. This presents a difficult challenge in distinguishing the two bands from each other.

In accordance with embodiments of the present disclosure, graph theory and dynamic programming may be used to generate two vertical gradient adjacency matrices for the mask: a black-to-white and a white-to-black adjacency matrix. The [−1;1] edge filter (notation corresponding to MATLAB's definition of vectors) may be used to create the black-to-white gradient image and the [1;−1] filter may be used to create the white-to-black gradient image, setting all values less than zero to zero. After automatic endpoint initialization, the image can be segmented twice searching for a black-to-white edge, and twice searching for a white-to-black edge. It is noted that as each layer have two, top and bottom boundaries (edges), therefore it requires the overall 4 searches described in above. In order to make sure the same edge is not segmented again, when segmenting subsequent edges, the corresponding nodes to the already segmented edge may be excluded. As can be seen in the example segmented image shown in FIG. 20, the borders successfully separate the NFL-OPL and IS-RPE complexes from each other.

Another detail to note is the possibility for the segmented lines to crisscross one-another, confusing the lower and upper bands with each other (e.g.: the lines 2000 and 2002 form an 'X' shape instead). Such a possibility may be managed by sorting the edge positions in each column once all four edges have been segmented, thus removing any crisscrossed edges.

3.4 Image Flattening via Convex Hull

The method of FIG. 18 includes image flattening 1806 via a convex hull technique. Initially, it is noted that the shortest path, i.e. the segmented line that has the overall least accumulative weight, is influenced by two independent mechanisms. That is, the preferred path is the one that passes through edges and nodes with low weights. Also, the preferred path has the tendency to pass thorough straight lines, as the curved paths pass through higher number of nodes and therefore accumulate a larger total weight. Therefore, the preferred path, in absence of strong anatomical gradients, has the tendency to short-cut the anatomical structure if it is curved. This is especially important for small drusen, with smooth edges. To remove this tendency, the structure to be segmented may be flattened. Flattening may be accomplished by obtaining a reference line (a layer boundary) to flatten, and by then shifting the columns of the image up or down until the reference line is entirely or substantially flat.

In retinal images with AMD, the most suitable reference line may be an imaginary convex line that encompasses the RPE layer. To estimate this line, the upper IS-RPE complex border generated from the binary mask may be used as the preliminary RPE. Next, the convex hull coordinates of the line may be found. The convex hull coordinates are the points on the line that fully enclose the remaining points while preserving a convex shape. FIG. 21 is an image showing an example convex hull 2100 encompassing a preliminary RPE line 2102.

For a convex retina where the sides curve upwards, or any other irregular retina shape other than concave, the lower convex hull coordinates may be utilized as the reference line estimate. For a fully concave retina where there are only two lower convex hull coordinates, the upper convex hull coordinates may be utilized as the reference line estimate. Since these upper coordinates can be influenced by pathology, this dependence may be reduced by fitting a fourth order curve to best estimate the reference line. After obtaining an estimate for the reference line, the entire image may be flattened by shifting the columns of the image up or down until reference line lies on a flat line or substantially flat line, as shown in the example of FIG. 22, which shows an image of a lower portion of the convex hull from FIG. 21 being used as the reference line estimate to flatten the retina, as designed by line 2200.

In accordance with embodiments of the present disclosure, the method of FIG. 18 includes calculating 1808 graph weights for the image, and segmenting 1810 layers.

3.5 RPE Flattening

Some flattening algorithms flatten the overall image rather than specific structures within the image. For example in retinal images, the entire retina is flattened to remove the overall curvature. When segmenting irregular structures, however, the overall flattened structure may not result in the shortest path for the specific anatomical structure we are interested in segmenting. This may result in unintended short-cuts when segmenting this specific structure.

For retinal images with AMD, for example, it is desired to segment the inner RPE+drusen complex boundary. While the convex hull technique resulted in a flattened retina (see the example of FIG. 23*a*), the resulting segmentation of the inner RPE+drusen border was incorrect (see the example of line 2300 shown in FIG. 23*b*) since short-cuts were taken instead of the intended path (i.e. taking an almost straight line, which is short and passes thorough a small number of nodes, rather than taking the curved path that is closer to anatomical structure).

Figure 23A:
FIG. 23a is an image showing image flattening using a reference line as the line to flatten.
Figure 23B:
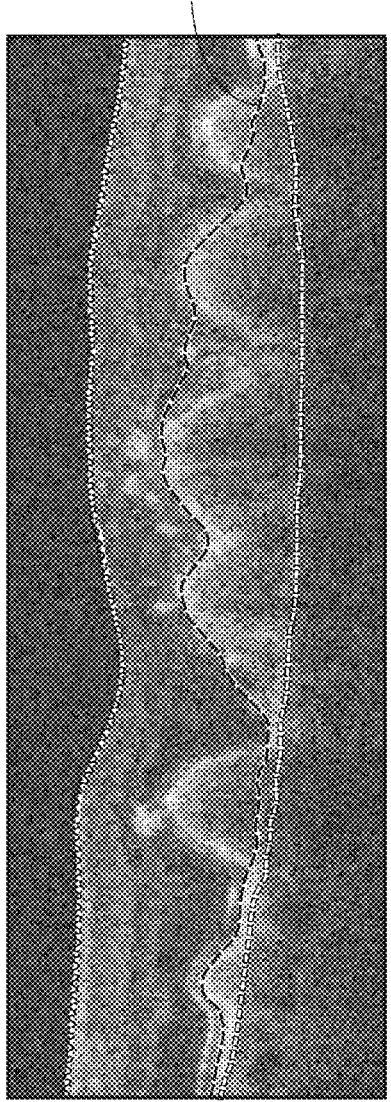
Figure 23C:
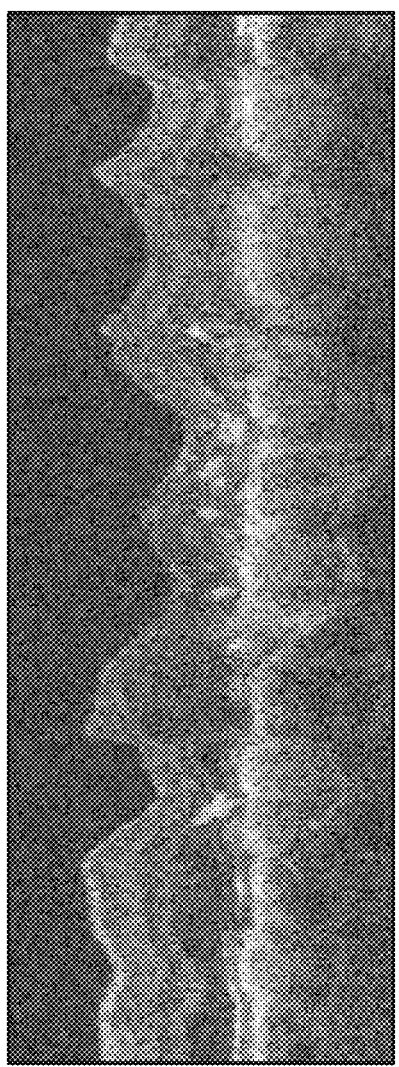
FIG. 23c is an image showing flattening using an RPE+ drusen estimate from a binary mask.
Figure 23D:
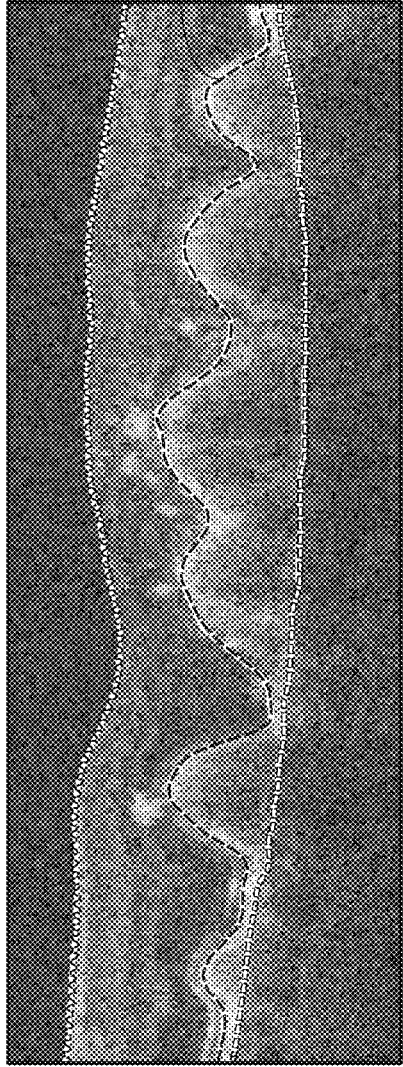
FIG. 23d is an image showing segmentation resulting from processing the image shown in FIG. 23 c.

For example, FIG. 23*a* is an image showing image flattening using a reference line as the line to flatten. The resulting segmentation of the image is shown in the example of FIG. 23*b*. FIG. 23*c* is an image showing flattening using the RPE+drusen estimate from the binary mask. FIG. 23*d* is an image showing a resulting segmentation.

To overcome such errors, we instead flatten the image based on the pilot RPE estimate generated from the binary mask. The resulting flattened image in shown in the example image of FIG. 23*c* shows an irregularly flattened retina different from the traditional retina flattening techniques. Since this flattened image shortens the path for the inner RPE+drusen border, the resulting segmentation is accurate (see the example of line 2302 shown in FIG. 23*d*). To clarify, the reference line may be used to segment the OS-RPE and IS-OS, while the reference line is used to segment other retinal layer boundaries, such as the vitreous-NFL or Bruch's membrane.

3.6 Structure Flattening with Image Mirroring

When flattening the image, the shifting of columns can introduce new pixels into the image without an assigned intensity value. These new pixels are invalid since they were not part of the original image. As a result, the corresponding nodes may be excluded from the adjacency matrix to prevent the algorithm from segmenting within these invalid regions.

If no intensity values are assigned to these new pixels, they can introduce artificial borders (See the example of FIG. 24*a*) in the image which may be later confused for the structure to segment (See the example of FIG. 24*b*). Note that even though these nodes can be excluded from the search region, a gradient may appear in the valid region of the image after filtering. To overcome this, the invalid regions are assigned intensity values corresponding to the mirror image of the values in the valid regions (See the example of FIG. 24*c*). This way when filtering, artificial borders will not be introduced and segmented in place of the intended structure (See the example of FIG. 24*d*).

Figure 24A:
FIG. 24a is an image showing flattening without mirroring.
Figure 24B:
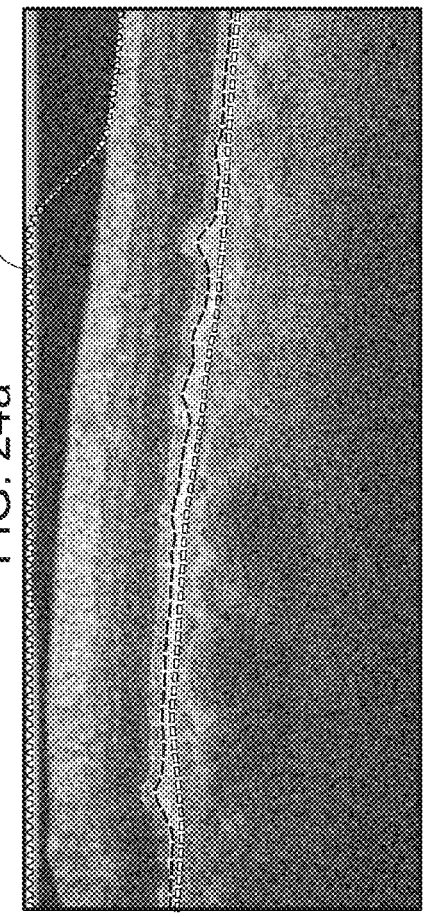
Figure 24C:
FIG. 24c is an image showing flattening after mirroring.
Figure 24D:
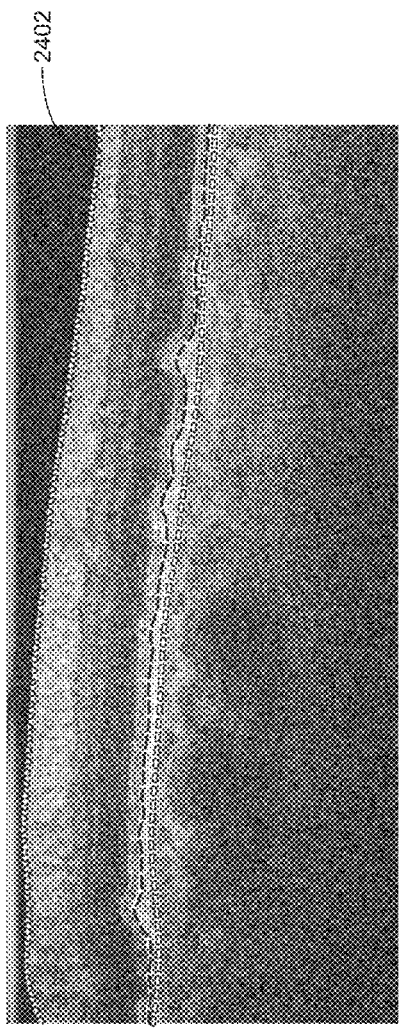
FIG. 24d is an image showing segmentation of the image of FIG. 24c.

FIG. 24*a* is an image of a flattened image without mirroring. FIG. 24*b* is an image showing resulting segmentation of the image shown in FIG. 24*a*. The error in segmenting the vitreous-NFL is shown by line 2400. FIG. 24*c* is an image showing flattening with mirroring. FIG. 24*d* is an image showing resulting segmentation of the image of FIG. 24*c*. In FIG. 24*d*, accurate segmentation of the vitreous-NFL is shown by line 2402.

3.7 Building a Default Shortest Path

Using the gradient of an image to build an adjacency matrix can be a useful technique for preferring the edge of a structure when finding the shortest path across an image. In cases where the structure does not have a clearly defined edge, however, the gradient weights may be critically small and the noise in the images may affect the edge segmentation accuracy. To address this issue, prior knowledge about the shape of the target structure can be utilized to customize the shape of the default shortest path (which is the path taken on a blank image) so it closely matches the corresponding anatomical structure. Therefore, in the absence of any structural information (e.g, in critically low signal-to-noise ratio regions of an image), the segmented line can follow the default shortest path, which matches the a priori assumed shape of the structure.

Figure 25A:
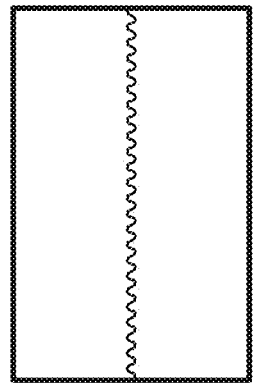
FIGS. 25a-25d are blank images including a preferred shortest path created by customizing edge weights based on position and distance according to embodiments of the present disclosure.
Figure 25B:
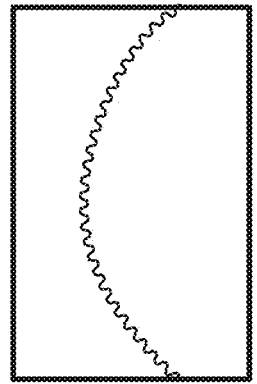
Figure 25C:
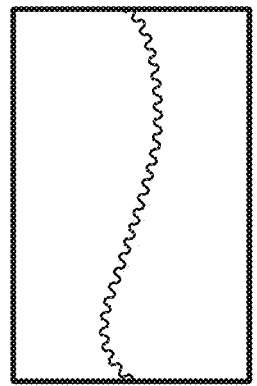
Figure 25D:
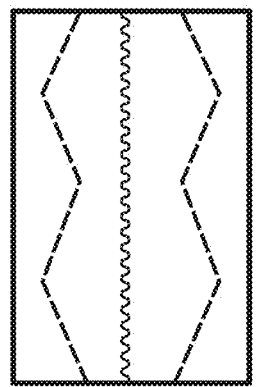

The a priori shortest path can be customized by changing the weights based on distance and position. For example if it is known that the structure is flat, then horizontal edge weights can be set to values lower than the diagonal edge weights (in the case that a minimum weight is preferred). Therefore for a blank image, the shortest path can be depicted by line 2500 in FIG. 25a, which illustrates a preferred shortest path on a blank image, created by customizing the edge weights based on position and distance. For curved structures, the diagonal edge weights can be set to the minimum along the outer regions of the image, and the horizontal edge weights can be set to the minimum in the central region of the image. This results in a curved shortest path (See the example of FIG. 25b) wherever no structural information is present. FIG. 25c is an image showing an example sinusoidal shortest path, however the path may take any shape or form. Lastly, if the shape of the structure is determined by the vertical position on the image, then the weights can be customized by height to prefer different paths. FIG. 25d is an image showing that if the path traverses across the top, middle, or bottom of a blank image, then it will prefer an upright zigzag, straight line, or upside-down zigzag shape, respectively.

Figure 26A:
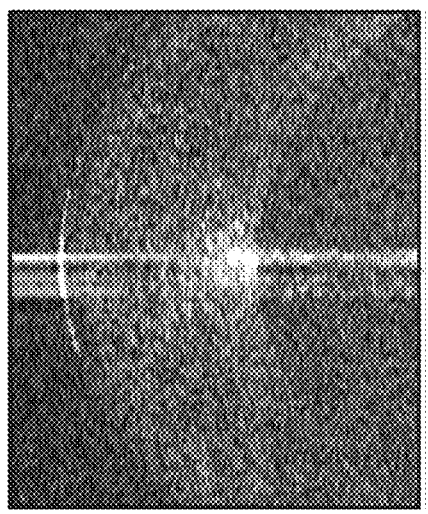
FIG. 26a is a corneal image with low SNR.
Figure 26C:
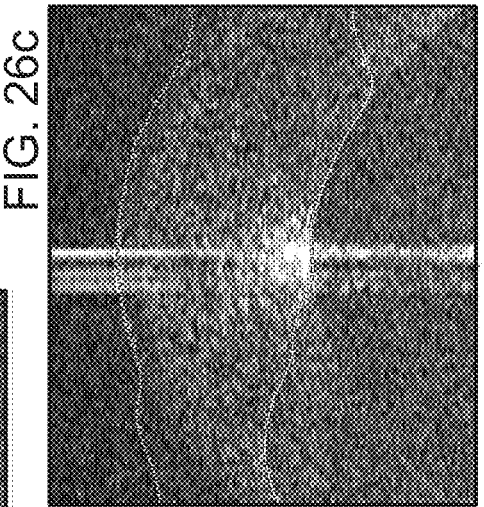
FIG. 26c is the image of FIG. 26a with a segmented path with concave shape weight preference.
Figure 26B:
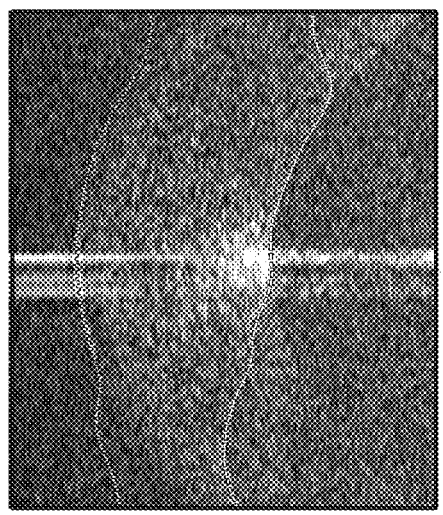
FIG. 26b is the image of FIG. 26a with a segmented path without a concave shape preference.

For corneal images where the cornea is always distinguished by a concave shape, the weights can incorporate distance weights (e.g., preferring diagonal versus horizontal edges) along with gradient weights to prefer a concave shape (See example of FIG. 25b) wherever structural content is lost. This is particularly useful when handling corneal images for several reasons. For instance, clinical corneal images can be of very low quality in either the entire image or in along the sides. For example, FIG. 26a is a corneal image with low SNR. When the signal-to-noise ratio of the entire image is very low, the algorithm will do its best to find an overall concave structure. For example, FIG. 10c is an image including a segmented path with concave shape weight preference. If the sides have a low SNR, then it will again look for structures that taper downwards instead of horizontally shortcutting the path. For example, FIG. 26b is an image showing a segmented path with concave shape weight preference.

Figure 27A:
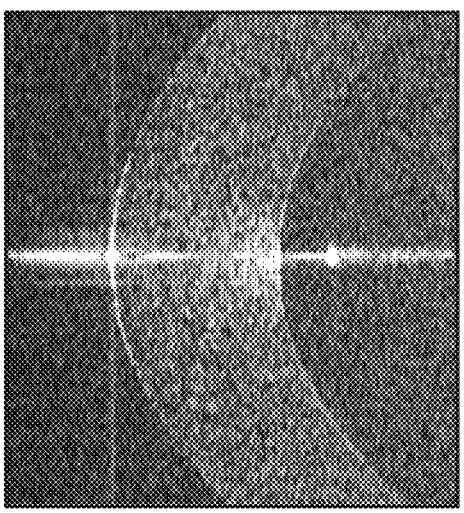
FIG. 27a is a corneal image with vertical and horizontal artifacts.
Figure 27C:
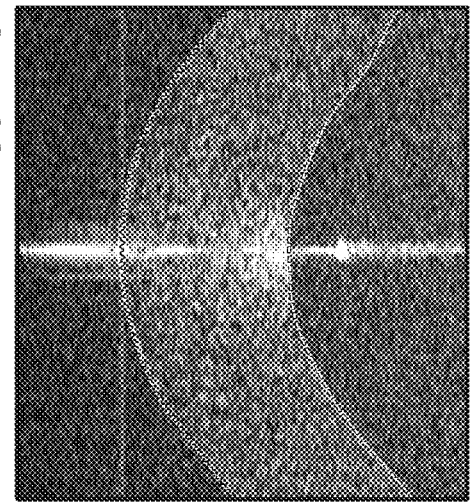
FIG. 27c is the image of FIG. 27a with a segmented path with concave shape weight preference.
Figure 27B:
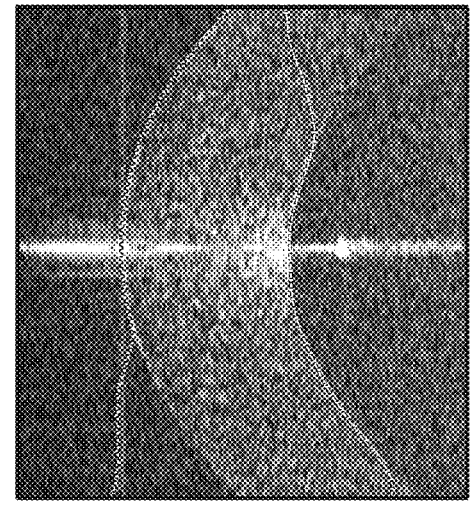
FIG. 27b is the corneal image of FIG. 27a with a segmented path without a concave shape preference.

In another instance, horizontal and vertical edge artifacts are often present on corneal images. For example, FIG. 27a is a corneal image with vertical and horizontal artifacts. Since they overlap with the cornea, they are more cumbersome to remove. However since the algorithm prefers curved structures, these artifacts will be ignored and do not need to be removed. The result is a segmented cornea instead of a mistakenly segmented artifact. FIG. 27b is an image showing a segmented path without concave shape preference. FIG. 27c is an image showing a segmented path with concave shape weight preference.

3.8 Combining Weights for Complex Structures

For structures that do not exhibit the same characteristics throughout, it may be difficult to segment the structure based on only a single trait. Therefore, several different weights may be combined to achieve an optimal weighting scheme that can best characterize all of the structure's qualities in accordance with embodiments of the present disclosure.

In retinal images, for example, drusen can be characterized by either a hyper or hypo-reflective bump sitting above or below the RPE. Without the presence of drusen, Bruch's membrane may be delineated by a light-to-dark gradient transition from the RPE to the choroid. With the presence of drusen under the RPE, however, the transition is no longer always light-to-dark. In cases with hypo-reflective drusen, the transition for Bruch's may be a dark-to-light gradient, or there is no transition at all, resulting in a Bruch's membrane that is not visible.

Figure 28A:
FIG. 28a is a retinal image with hyper and hypo-reflective drusen.
Figure 28B:
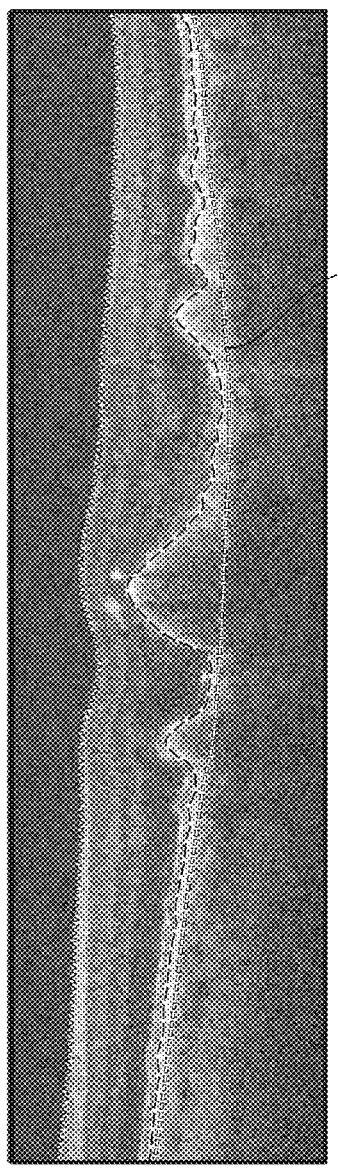
FIG. 28b is the image of FIG. 28a with a segmented Bruch's membrane using a combination of distance, light-dark gradient, dark-light gradient, and intensity weights.

To address the variability in the RPE-choroid boundary, light-dark gradient, dark-light gradient, distance, and intensity weights may be combined to successfully segment Bruch's membrane. First, the image was already flattened with respect to the estimated reference line, distance weights may be used to prefer a horizontal path as depicted in FIG. 28a. This allows for the areas where Bruch's membrane is not visible to be segmented correctly. The light-dark gradient weights may be included to locate Bruch's in areas where there are no druse or hyper-reflective druse. As a counterintuitive step, we add dark-light gradient weights to locate hypo-reflective druse. Lastly, in the presence of geographic atrophy (GA), intensity weights may be added since Bruch's is characterized by a thin, bright line. The result is an accurately segmented Bruch's membrane as indicated by line 2800 shown in FIG. 28b.

3.9 Segmenting Clipped Layers

A technique for automatic endpoint initialization in accordance with embodiments of the present disclosure may assume that the structure of interest spans the entire width of the image. In several cases, however, the structure may not follow this assumption. If this is the case, the structure may be segmented under the assumption that it fills the width of the image. Next, information about the structure may be used to remove the segmented line wherever it does not lie along the structure of interest.

Figure 29A:
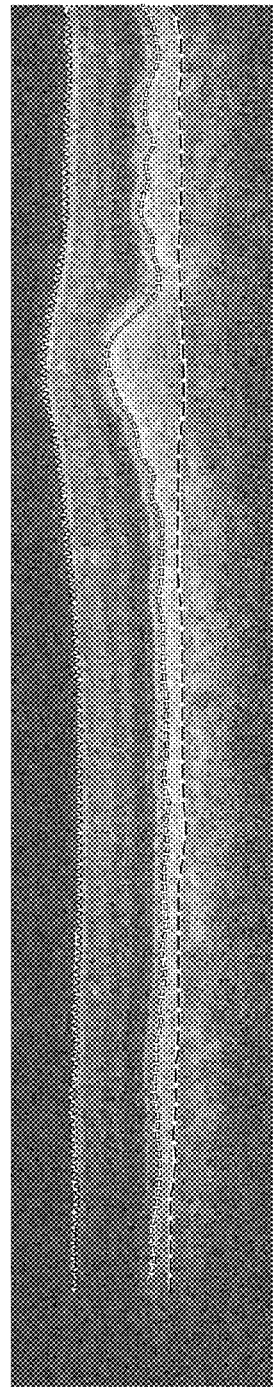
FIG. 29a is a retinal image that has been segmented where all layers have been clipped due to a lack in signal.
Figure 29B:
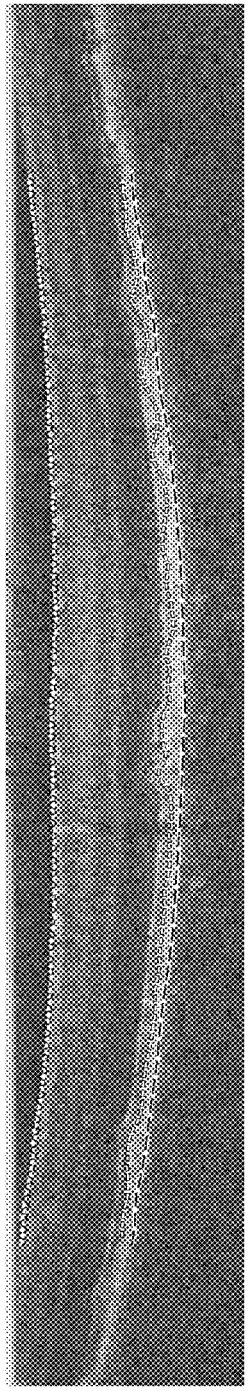
FIG. 29b is a retinal image that has been segmented where the vitreous-NFL layer boundary has been cut off.

For retinal images, the retina is often clipped at the edges due to either a lack or cutoff in the signal. In both cases, each layer may be segmented under the assumption that it spans across the entire image. Next, a search may be performed for columns at either end of the image with a signal-to-noise ratio (SNR) well below the mean. If any columns exhibit a low SNR, the segmented lines in those columns may be removed. For example, FIG. 29a is a segmented retinal image where all layers have been clipped due to a lack in signal. For layers that have been cut-off, such as the vitreous-NFL layer as depicted in the segmented retinal image of FIG. 29b, the segmented line may drop down to the next layer similar in characteristics (e.g. the INL-OPL layer boundary). Since the retina has already been flattened, the vitreous-NFL should be relatively horizontal. Therefore, search on both sides of the image may be performed for a large jump down in the segmented layer and remove the segmented line in those regions (See the example of FIG. 29b). It is noted that this is only one proposed technique of several that may be utilized, such as such as an intensity profiling technique.

3.10 Segmenting via Sparse Search Region Limitation

An important step to accurately segment a structure is to appropriately limit the search region. This allows for the structure of interest to be isolated from other features that may be confused with the structure to segment. Oftentimes, however, accurate search region limitation can be difficult. As an alternative to thoroughly limiting the search space, sparse search region limitation may be used instead. By restricting the search region in only a few locations, the resulting segmentation of the entire line may be changed.

Figure 30A:
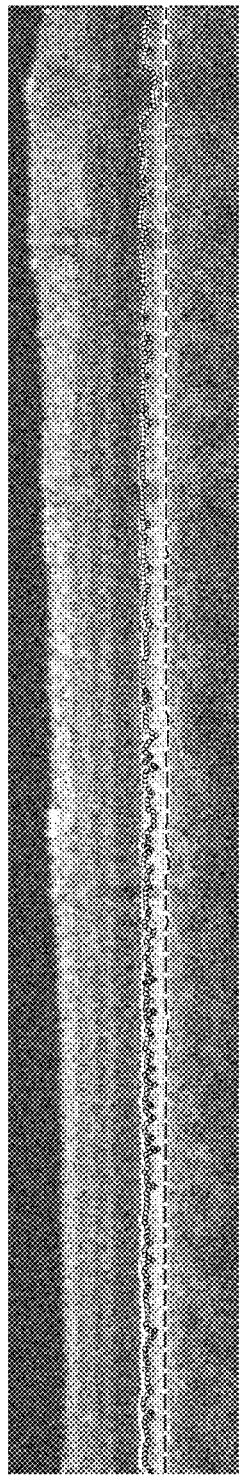
FIG. 30a is an image showing a sparse search region limitation.
Figure 30B:
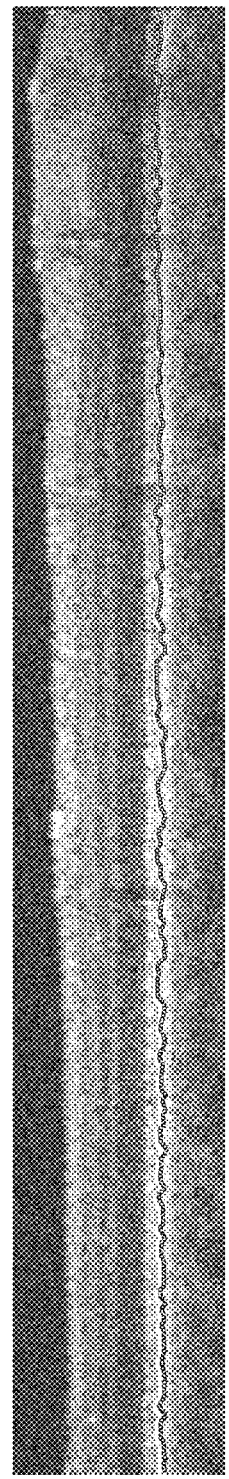
FIG. 30b is the image of FIG. 30a after segmentation.

For retinal images, the IS-OS and OS-RPE layer boundaries are similar structures and reside in close proximity to each other. These two layer boundaries are therefore often confused with each other when segmenting, or merged together resulting in an indistinct separation between the two boundaries. Accurately isolating one region from the other can therefore be difficult. By only limiting the search region whenever possible, an accurate graph cut can still be achieved. It is desired to segment the OS-RPE layer boundary. With the IS-OS and RPE-choroid boundaries already segmented, the search region can be limited to those two regions. To prevent the subsequent graph cut from segmenting the IS-OS again, however, the entire image may be smoothed with a Gaussian filter, for example. Next, a column-wise search may be performed for the OS-RPE by locating a minimum intensity in between the confining layer boundaries. If a minimum is detected, the top layer boundary may be pushed down to the minimum value. This can be seen in the example of FIG. 30*a* by the sharp drops down in the top layer boundary. Although the search region of the top boundary is only sparsely limited to isolate the IS-OS from being re-segmented, the resulting graph cut shown in FIG. 30*b* successfully finds the OS-RPE layer boundary.

3.11 Segmenting via Structure Categorization

To develop an algorithm that segments a wide variety of image types, special handling for the variations in the same feature may be necessary. In some weighting schemes used to segment a structure of varying qualities, the variations may be too large from one image to another that an entirely different weighting scheme is needed. In this case, we use prior information about the structure to detect which attribute is most prominent, and use the corresponding adjacency matrix to successfully segment the structure. As an alternative technique to weight customization, the search regions can be limited differently.

For retinal images with AMD pathology, the characteristics of the Bruch's membrane layer boundary are noticeably different when segmenting images containing drusen versus GA. In images with drusen, Bruch's membrane is most noticeable by a gradient change, whereas in images with GA, Bruch's membrane is clearly seen by a thin, hyper-reflective layer with hyper-reflective bands underneath. To more accurately segment this layer, Bruch's membrane may be tentatively segmented using a general weighting scheme as disclosed herein. The pixels within a certain range below the structure may be summed and the maximum intensity compared with the minimum intensity. If the difference is greater than a predetermined threshold, it may be concluded that GA is present in the image. Otherwise, it may be assumed that only drusen is present in the image. Next, the structure of interest may be re-segmented using either customized weights (in this case, the intensity weights may be increased for image with GA, and lower the intensity weights for images with drusen), or customize the search region accordingly (here, the lower region boundary may be limited for images with GA to prevent the hyper-reflective choroid from being confused for Bruch's, and the upper region boundary may be limited for images with drusen to prevent the outer RPE from being segmented).

3.12 Segmenting Disappearing Structures

Figure 31:
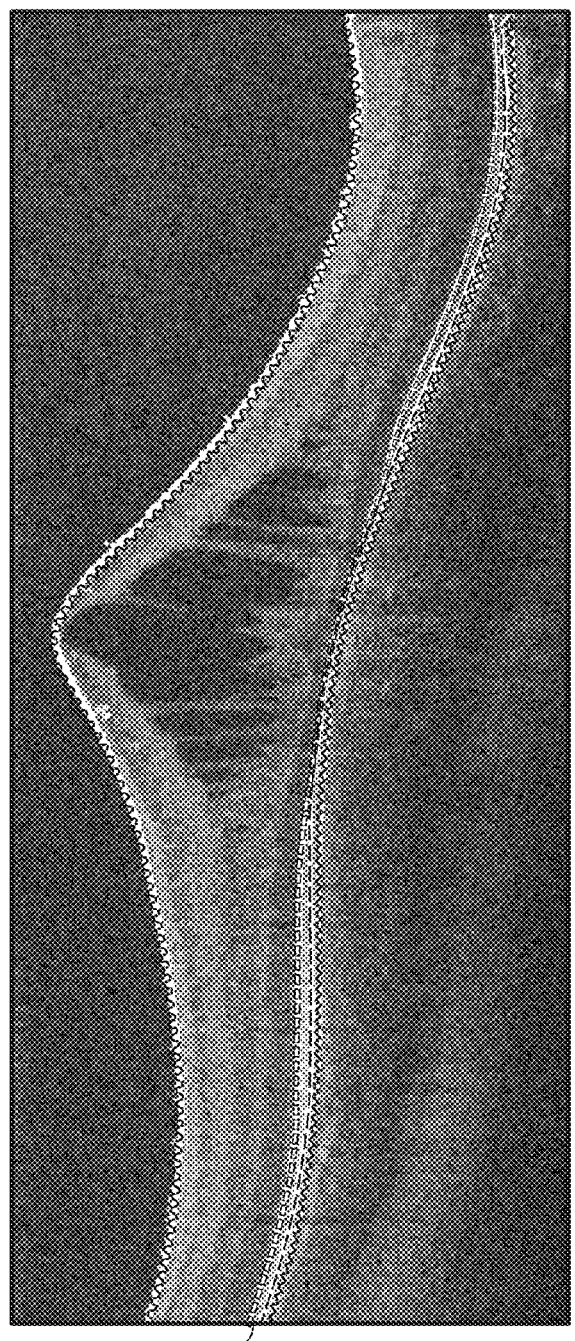
FIG. 31 is an image having a disappearing IS-OS boundary.

There may be scenarios where the structure of interest is not fully continuous across the entire width of the image. The cause of this may be due to anatomy, imaging properties, or other reasons. With retinal images, the outer segments are not always present above the RPE layer, resulting in an IS-OS boundary that appears and disappears into the OS-RPE boundary. Noting that the OS is a thin structure residing above the RPE layer, and that the RPE layer does not disappear, the OS-RPE may be segmented since it is more reliable boundary than the potentially disappearing IS-OS. Next, the lower boundary of the search region may be set to reside a few pixels above the OS-RPE boundary to ensure the layer is not re-segmented. The upper search region boundary may then be set to a fixed height above the bottom boundary, which can be determined based on knowledge of the OS thickness. Segmentation may be performed across this search region. Further, it may be determined whether the IS-OS boundary was found based on the distance from the IS-OS to the OS-RPE. If the thickness is close to the expected OS thickness, then the OS is present. If the OS is not present, then the segmentation should have dropped down to the lower boundary of the search region. Therefore, any points may be replaced along the IS-OS segmentation with an OS thickness less than the acceptable threshold to the OS-RPE boundary, thus effectively locating the disappeared OS locations. This is shown in the example of FIG. 31, where line 3100 is present on either side of the elevated edema pathology, and disappeared in the central region. FIG. 31 is a segmented pediatric SCOCT image with a disappearing IS-OS layer boundary.

4 Experimental Results

4.1 Automated Versus Manual Segmentation Study

To determine the accuracy of an eight retinal layer boundary segmentation method on SDOCT images in accordance with embodiments of the present disclosure, an automatic versus manual segmentation study was conducted. This study included macular scans from normal adult subjects segmented manually by an expert grader and automatically using software implementing the method on a computer. To estimate inter-expert-observer variability, a subset of scans was graded manually by a second expert. Both expert graders were certified OCT readers certified.

Volumetric scans (6.7×6.7 mm) were acquired from 10 normal adult subjects in an Institutional Review Board (IRB) approved protocol using SDOCT imaging systems with an axial full-width at half-maximum (FWHM) resolution of 4.6 µm (in tissue) and an axial pixel sample spacing of 3.23 µm. Five of the volumetric scans had lateral and azimuthal pixel sampling spacings of 6.7 µm and 67 µm (1000 A-scans×100 B-scans), respectively. The other 5 volumetric scans had resolutions of 13.4 µm and 33.5 µm (500 A-scans×200 B-scans) to validate the algorithm on varying lateral and azimuthal image resolutions. It is noted that the volumetric scans were comprised of a series of cross-sectional images, or B-scans, where the number of A-scans represents the image width.

To compare the automatic versus manual segmentation results, 11 B-scans from each data set were selected with the sixth B-scan centered at the fovea and subsequent B-scans departing from the fovea at a linear rate. The inter-expert comparison included a subset of 3 B-scans from each set of 11 B-scans. The three B-scans chosen from each set included the foveal scan and two other randomly selected B-scans. Due to a prominent, irregular imaging artifact in one of the B-scans and a gross manual segmentation error in another B-scan, a total of two B-scans were removed from the study. Furthermore, 8 B-scans were used as training data for bias correction as will be described below. As a result, 100 B-scans (10

B-scans per data set) were observed for the automatic versus manual comparison and a subset of 29 B-scans (3 B-scans per data set with the exception of one) were included in the inter-expert comparison.

Prior to automatic segmentation, ten percent of the image width was cropped from either side of each image to remove regions with low signal. Eight retinal layer boundaries were segmented automatically on 108 B-scans using a MATLAB software implementation of our algorithm. The average computation time was 9.74 seconds per image (64-bit OS, Intel Core2 Duo CPU at 2.53 GHz, and 4 GB RAM). The same eight layers were manually traced by two expert graders for the subset of 29 B-scans. Furthermore, the certified graders traced layers using their own expertise and were not allowed to consult with each other.

In order to closely match the segmentation results of an expert grader, the automatic segmentation results were smoothed using a moving average filter. This was necessary because the automatic algorithm tightly followed gradient changes, whereas manual segmentation tended to be smooth. Furthermore, each expert grader exhibited a bias when tracing layer boundaries, either consistently following above or below by a constant distance from the actual boundary. As a result, training was performed on the 8 test images to determine any segmentation biases from the manual grading. Each automatically segmented layer in the set of 100 B-scans was then shifted up or down by bias values of −0.9, −0.8, −1.0, −1.3, −1.6, −1.3, −0.3, and −0.6 pixels, respectively, in order to mimic the segmentation behavior of the manual grader.

Upon smoothing the layers and correcting for bias, the thicknesses of the 7 retinal layers were calculated for each of the 100 B-scans between neighboring layer boundaries. The average difference in layer thickness between the manual and automatic estimates was computed for each layer of each B-scan. The same was done to compare the two manual expert graders for 29 B-scans. The absolute mean and standard deviation of these differences across all B-scans were calculated and are shown in below. Column I of the table shows the absolute average thickness difference for the various retinal layers as measured by two expert manual graders for 29 B-scans. Column II of the table displays the same layer thickness difference calculation for the 29-Bscans, but with layer thicknesses determined by the automatic segmentation software and one of the two manual graders. Column III of the table reports the thickness differences between the automatic and manual grader for the larger set of 100 B-scans. Each pixel is 3.23 μm.

TABLE 1

Retinal Layer Thickness Differences

| | Comparison of Two Manual Expert Graders | | Comparison of Automatic and Manual Segmentation | | | |
|---|---|---|---|---|---|---|
| | Column I | | Column II | | Column III | |
| | 29 B-scans | | | | 100 B-scans | |
| Retinal Layer | Mean Difference (Pixels) | Standard Deviation (Pixels) | Mean Difference (Pixels) | Standard Deviation (Pixels) | Mean Difference (Pixels) | Standard Deviation (Pixels) |
| NFL | 1.73 | 0.90 | 0.99 | 0.76 | 0.88 | 0.68 |
| GCL-IPL | 1.06 | 0.95 | 0.57 | 0.48 | 0.77 | 0.65 |
| INL | 2.22 | 1.30 | 1.07 | 0.87 | 0.98 | 0.74 |
| OPL | 1.90 | 1.53 | 1.64 | 1.08 | 1.48 | 1.05 |
| ONL-IS | 1.63 | 1.19 | 1.40 | 1.06 | 1.20 | 0.92 |
| OS | 1.11 | 0.88 | 0.92 | 0.80 | 0.88 | 0.73 |
| RPE | 2.21 | 1.20 | 0.96 | 0.69 | 0.99 | 0.87 |
| Total Retina | 2.22 | 1.00 | 0.92 | 0.83 | 0.94 | 0.82 |

Among all datasets, maximum differences for the 8 retinal thicknesses reported in columns I and II of Table 1, (Column I, Column II), were as follows: NFL (10,18.7), GCL-IPL (11,11.8), INL (12,9.7), OPL (11,15.2), ONS-IS (10,11.1), OS (8,7.6), RPE (11,7.9), and total retina (11,12).

Figure 16:
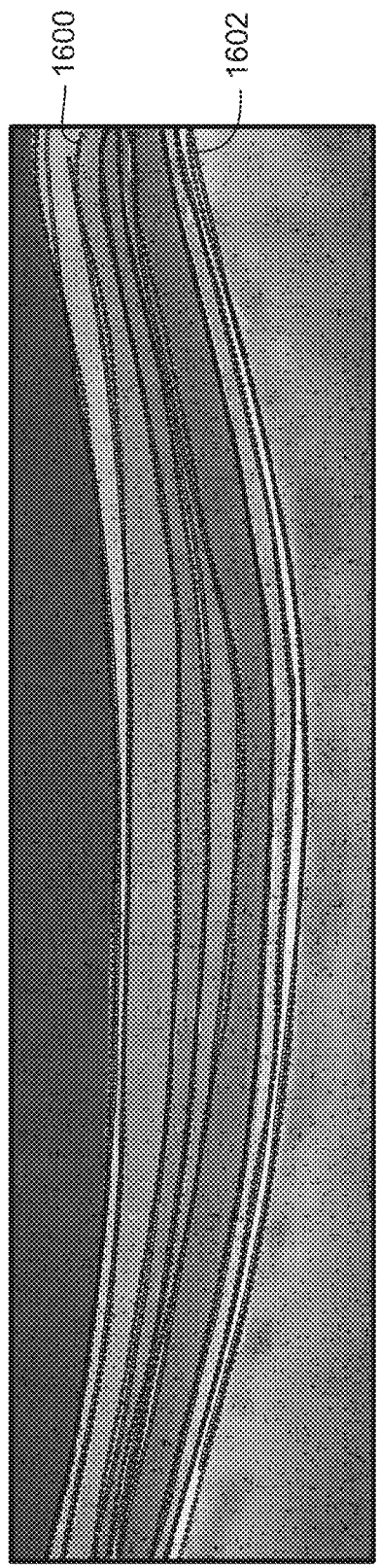
FIG. 16 is an image showing a comparison of automatic versus manual segmentation.

The results in show that the automatic algorithm accurately segmented seven retinal layers in normal adult eyes more closely to an expert grader as compared to another grader. For example, two manual graders differed in their segmentation of the total retina by an average of 2.22 pixels, whereas our fully automatic algorithm differed from one of the manual graders by an average of 0.95 pixels. FIG. 16 is an image showing a comparison of automatic versus manual segmentation. In FIG. 16, the automatic segmentation, designated 1600, overlaid with the manual segmentation, designated 1602, results.

To test the repeatability of this method, we captured five volumetric scans of one normal subject with lateral and azimuthal pixel sampling spacings of 6.7 μm and 67 μm (1000 A-scans×100 B-scans), respectively. The subject rested between each volumetric imaging. In accordance with long-standing clinical convention, the volume of each retinal layer in the 3 mm diameter circle around the fovea was calculated. One of these scans was selected as anchor and compared the automatically measured volume of each of its layers with those of the other scans. Further, the normalized mean and standard deviation of the differences were calculated in estimating the volume of each layer. The results, (mean, standard deviation), were as follows: NFL (3.88%,3.43%), GCL-IPL (1.70%,1.99%), INL (3.37%,3.43%), OPL (2.20%,2.01%), ONS-IS (1.02%,0.76%), OS (0.84%,0.61%), RPE (0.16%, 0.18%), and total retina (0.26%,0.09%). It is noted that, such slight differences are mainly due to the uncontrollable patient motion during the volumetric scans and existence of significant preretinal image artifacts in some of the captured B-scans.

4.2 Other Segmentation Results

Figure 17A:
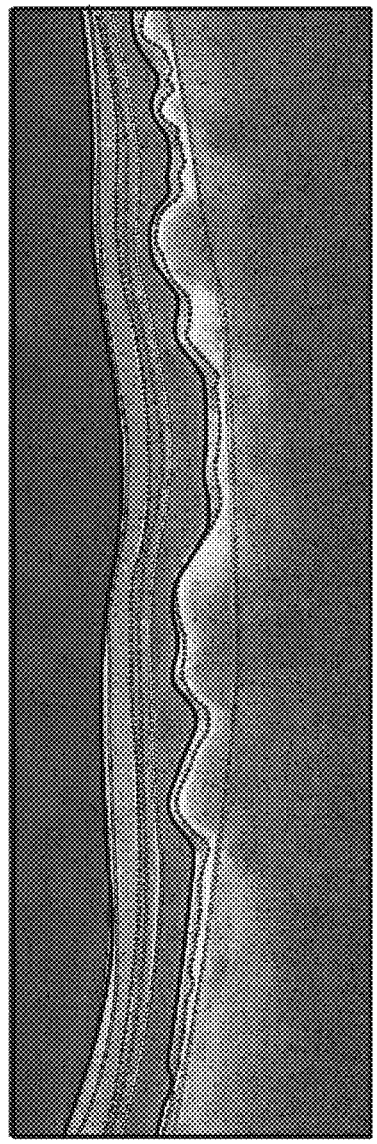
FIGS. 17a-17f are segmentation of anatomical and pathological images of the eye obtained by a method in accordance with embodiments of the present disclosure.
Figure 17D:
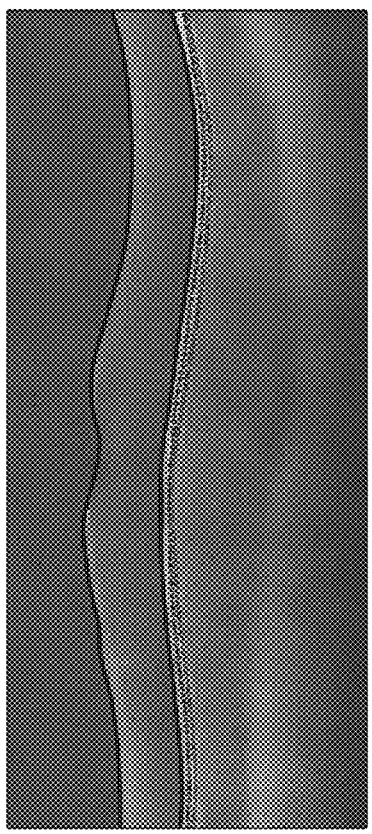
Figure 17B:
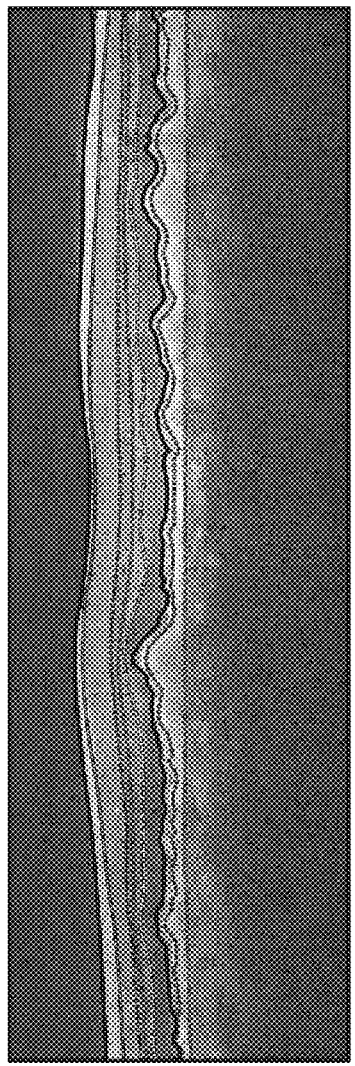
Figure 17E:
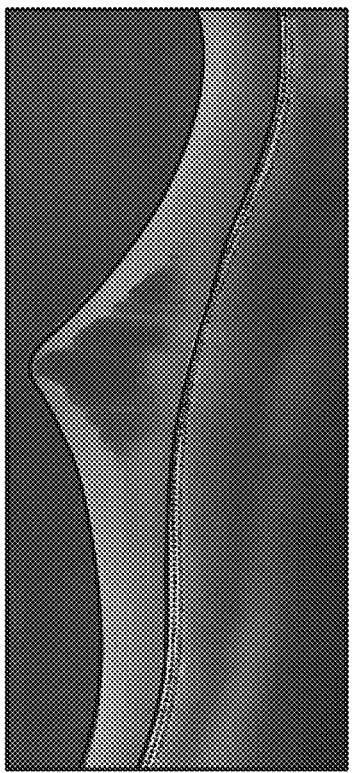
Figure 17C:
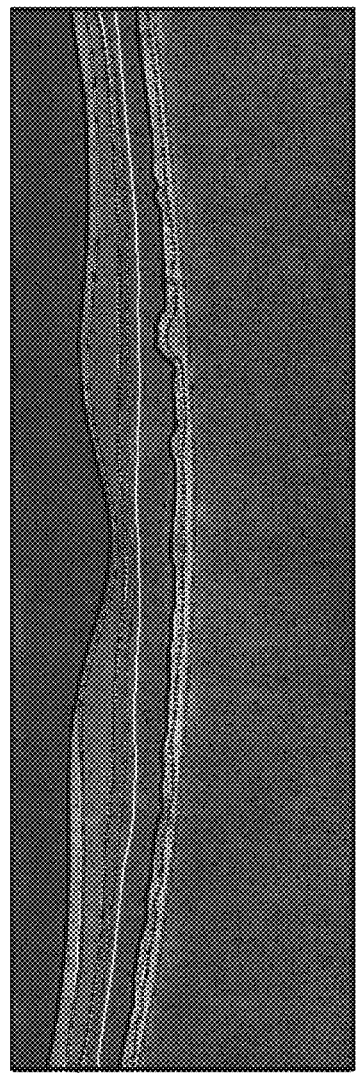
Figure 17F:
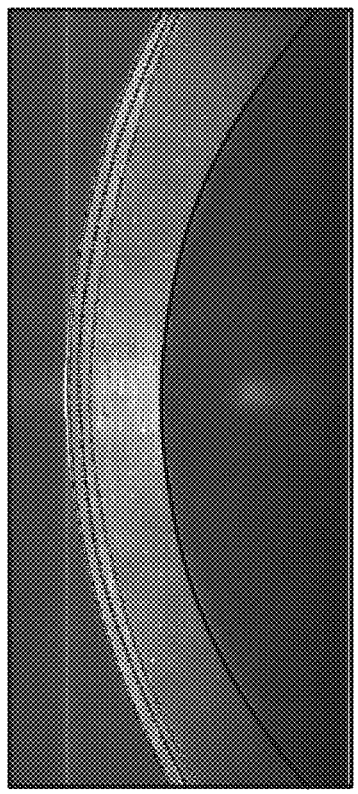

Sections 2 and 2.1 describe a method according to embodiments of the present disclosure implemented for segmenting retinal layers on macular, normal adult SDOCT images. The method in Section 1 for different types of layered structure. FIGS. 17a-17f are segmentation of anatomical and pathological images of the eye obtained by a method in accordance with embodiments of the present disclosure. Particularly, FIGS. 17a-17f show the segmentation results for a variety of SDOCT image types, including retinas with Level 3 aged-macular degeneration are shown in FIGS. 17a and 17b, a retina with Level 3 AMD with poor image quality is shown in FIG. 17c, a pediatric retina is shown in FIG. 17d, a pediatric retina with edema is shown in FIG. 17e, and the cornea is shown in FIG. 17f.

The automatic algorithm accurately segmented eight retinal layer boundaries on SDOCT images of normal eyes, with consistent results that matched an expert grader more closely than a second grader. This is highly encouraging for both reducing the time and manpower required to segment images in large-scale ophthalmic studies.

System and method embodiments of the present disclosure may also be applied to other ocular imaging scenarios, including pathological eyes, pediatric eyes, corneal images, and images from other SDOCT systems. To achieve this, weighting schemes in addition to vertical gradients, such as distance penalties, can be included in adjacency matrix calculations, and alternative approaches for search space limitation can be implemented. In addition, since the particular techniques disclosed herein target 2-D image segmentation, information from neighboring B-scans can be utilized in correcting for outliers, or methods according to embodiments of the present disclosure can be readily extended to 3-D segmentation (indeed with a significant increase in computational complexity). To make the disclosed systems and methods more suitable for use in clinic, its computational complexity may be reduced. This may be achieved by utilizing efficient computer programming languages (e.g. C instead of MATLAB) and taking advantage of the Graphics Processing Units (GPUs). To reduce filter smoothing artifact, especially for thin retinal layers, it may be beneficial to use non-linear adaptive filters for image denoising and edge detection.

4.3 AMD Results

In one study, a total of 108 macular B-scans from 10 normal adult subjects were segmented manually by one grader and automatically using our method. To estimate inter-expert-observer variability, a subset of 29 B-scans was graded manually by two experts. The average thickness of 7 retinal layers in each B-scan was measured. The absolute value difference of the average layer thicknesses between the manual was calculated and estimated. The mean and standard deviation of these differences across all B-scans are compared in Table 2.

A total of 20 volumes with non-neovascular AMD were selected with 10 volumes containing drusen and 10 including GA. Each of the 10 datasets had five good and five low quality volumes. Eleven B-Scans from each volume were segmented manually by two expert graders and automatically using our software. The study involved calculating the absolute value mean difference and standard deviation of the automatic segmentation as compared to one manual grader was comparable to that of a second grader, and the results are shown in Table 2 below.

TABLE 2

Retinal Boundary Differences
Retinal Boundary Differences

| Pathology | Quality | Retinal Layer Boundary | Comparison of Two Manual Expert Graders (Column I) | | Comparison of Automatic and Manual Segmentation (Column II) | |
|---|---|---|---|---|---|---|
| | | | Mean Difference (Pixels) | Standard Deviation (Pixels) | Mean Difference (Pixels) | Standard Deviation (Pixels) |
| Drusen | High | Vitreous – NFL | 0.73 | 0.80 | 0.80 | 0.38 |
| | | Inner RPE + Drusen | 1.28 | 1.19 | 0.66 | 0.49 |
| | | Outer RPE + Drusen | 0.72 | 0.64 | 0.66 | 0.54 |
| | Low | Vitreous – NFL | 0.56 | 0.40 | 0.61 | 0.44 |
| | | Inner RPE + Drusen | 0.91 | 0.83 | 1.01 | 0.89 |
| | | Outer RPE + Drusen | 0.99 | 0.82 | 0.89 | 0.74 |
| GA | High | Vitreous – NFL | 0.48 | 0.37 | 0.54 | 0.36 |
| | | Inner RPE + Drusen | 1.29 | 1.28 | 1.18 | 0.92 |
| | | Outer RPE + Drusen | 0.90 | 0.78 | 1.56 | 1.24 |
| | Low | Vitreous – NFL | 0.59 | 0.38 | 0.77 | 0.47 |
| | | Inner RPE + Drusen | 0.86 | 0.71 | 1.25 | 0.75 |
| | | Outer RPE + Drusen | 0.83 | 0.64 | 0.89 | 0.66 |
| Total | | Vitreous – NFL | 0.59 | 0.52 | 0.68 | 0.43 |
| | | Inner RPE + Drusen | 1.09 | 1.04 | 1.03 | 0.81 |
| | | Outer RPE + Drusen | 0.86 | 0.73 | 1.00 | 0.90 |

Figure 32A:
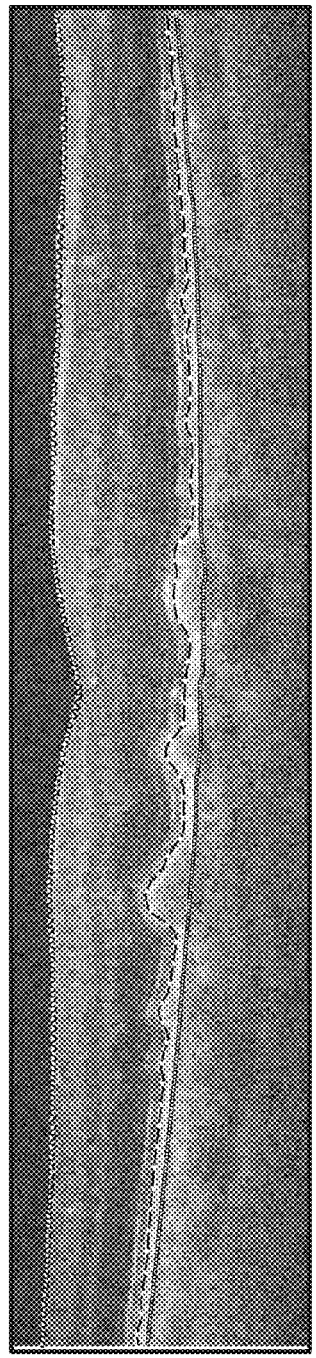
FIGS. 32a-32d are segmented high and low quality images containing drusen or GA.
Figure 32B:
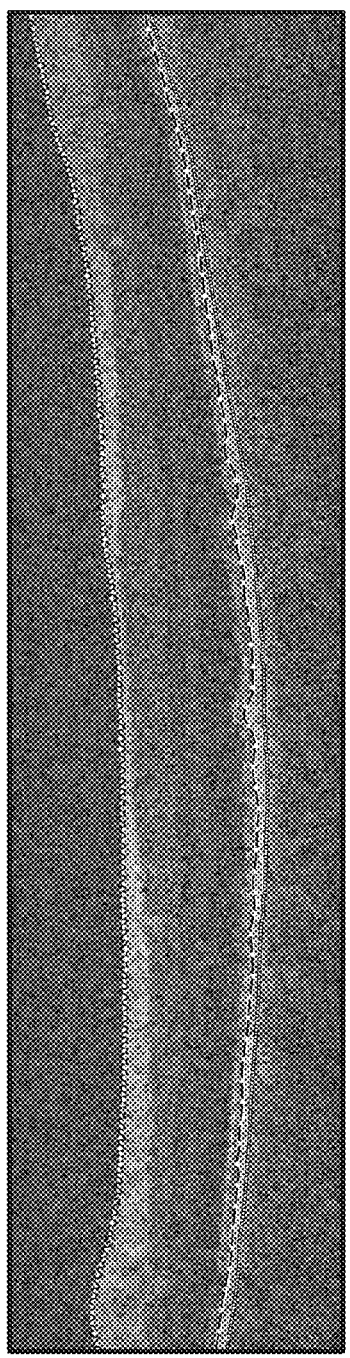
Figure 32C:
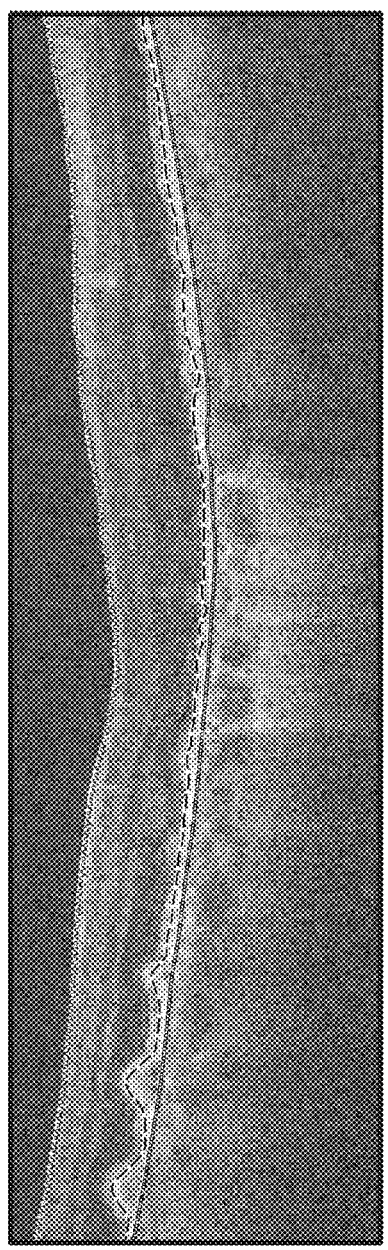
Figure 32D:
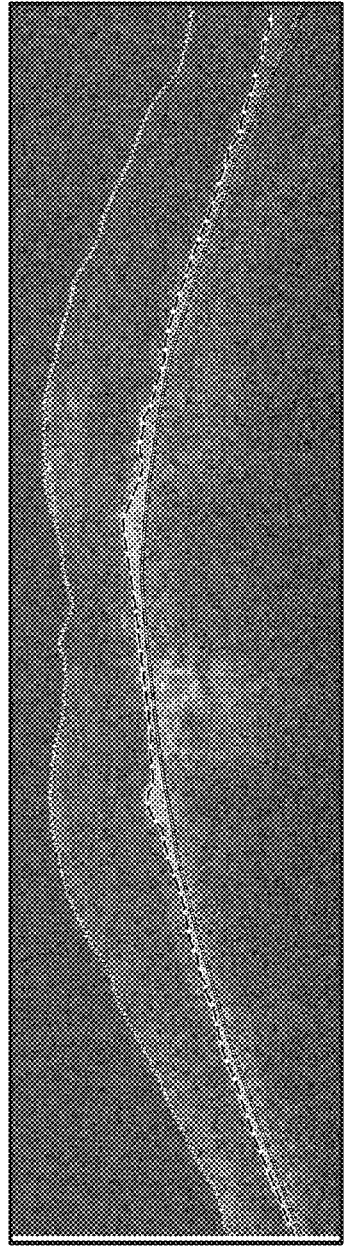

An example segmented high and low quality image containing either drusen or GA are shown in FIGS. 32a-32d. FIG. 32a is a segmented high quality drusen image. FIG. 32b is a segmented low quality image. FIG. 32c is a segmented high quality GA image. FIG. 32d is a segmented low quality GA image.

5 Example Systems, Methods, and Computer Program Product for Implementing the Presently Disclosed Subject Matter As will be appreciated by one skilled in the art, aspects of the presently disclosed subject matter may be embodied as a system, method or computer program product. Accordingly, aspects of the presently disclosed embodiments may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the presently disclosed embodiments may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium (including, but not limited to, non-transitory computer readable storage media). A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the presently disclosed embodiments may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter situation scenario, the remote computer may be connected to the user's computer through any type of network, including a local area network (LAN) or a wide area network (WAN), or the connection may be made to an external computer (for example, through the Internet using an Internet Service Provider).

Aspects of the presently disclosed embodiments are described below with reference to flow chart illustrations and/or diagrams of methods, apparatus (systems) and computer program products according to embodiments of the present disclosure. For example, aspects of the present subject matter are described with reference to the flow charts of FIGS. 2, 5, and 18. It will be understood that each block of the flow chart illustrations and/or diagrams, and combinations of blocks in the flow chart illustrations and/or diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flow chart and/or diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flow chart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flow chart and/or block diagram block or blocks.

The flow chart and block diagrams in the Figures illustrate the architecture, functionality, and operation of possible implementations of systems, methods and computer program products according to various embodiments of the presently disclosed subject matter. In this regard, each block in the flow chart or block diagrams may represent a module, segment, or portion of code, which comprises one or more executable instructions for implementing the specified logical function(s). It should also be noted, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flow chart illustration, and combinations of blocks in the block diagrams and/or flow chart illustration, can be implemented by special purpose hardware-based systems that perform the specified functions or acts, or combinations of special purpose hardware and computer instructions. The terminology used herein is for the purpose of describing particular embodiments only and is not intended to be limiting of the present disclosure. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the presently disclosed embodiments has been presented for purposes of illustration and description, but is not intended to be exhaustive or limited to the embodiments in the form disclosed. Many modifications and variations will be apparent to those of ordinary skill in the art without departing from the scope and spirit of the presently disclosed subject matter. The embodiment was chosen and described in order to best explain the principles of the present subject matter and the practical application, and to enable others of ordinary skill in the art to understand the present disclosure for various embodiments with various modifications as are suited to the particular use contemplated.

What is claimed:

1. A method comprising:
representing an image as a graph of nodes connected together by edges, wherein the image includes first and second layered features;
identifying nodes corresponding to first and second layered features;
determining intensities of pixels of the image; and
determining positions of nodes of the graph corresponding to other layered features based on the determined intensities of the pixels and the determined positions of nodes corresponding to the first and second layered features, and
wherein determining positions of nodes of the graph corresponding to other layered features comprises graph cutting the graph of nodes, wherein a search associated with the graph cutting is limited to a region of the graph that excludes the nodes corresponding to first and second layered features.

2. The method of claim 1, wherein the layered features are retinal layer boundaries.

3. The method of claim 1, wherein identifying nodes corresponding to first and second layered features comprises graph cutting the graph of nodes.

4. A computer-implemented system comprising:
at least one processor and memory configured to:
represent an image as a graph of nodes connected together by edges, wherein the image includes first and second layered features;
identify nodes corresponding to first and second layered features;
determine intensities of pixels of the image; and
determine positions of nodes of the graph corresponding to other layered features based on the determined intensities of the pixels and the determined positions of nodes corresponding to the first and second layered features, and
wherein the processor and memory are configured to graph cut the graph of nodes, wherein a search associated with the graph cutting is limited to a region of the graph that excludes the nodes corresponding to first and second layered features.

5. The system of claim 4, wherein the processor and memory are configured to graph cut the graph of nodes.

* * * * *